US008445215B1

(12) United States Patent
Wang et al.

(10) Patent No.: US 8,445,215 B1
(45) Date of Patent: May 21, 2013

(54) ASSAYS AND METHODS FOR THE DETECTION OF CROHN'S DISEASE

(75) Inventors: Shui-Long Wang, San Diego, CA (US); Nicholas Chi-Kwan Ling, San Diego, CA (US); Sharat Singh, Rancho Santa Fe, CA (US)

(73) Assignee: Nestec S.A., Vevey (CH)

( * ) Notice: Subject to any disclaimer, the term of this patent is extended or adjusted under 35 U.S.C. 154(b) by 65 days.

(21) Appl. No.: 13/190,369

(22) Filed: Jul. 25, 2011

Related U.S. Application Data

(60) Provisional application No. 61/367,328, filed on Jul. 23, 2010.

(51) Int. Cl.
*G01N 33/53* (2006.01)

(52) U.S. Cl.
USPC .......................................... 435/7.1; 436/518

(58) Field of Classification Search
None
See application file for complete search history.

(56) References Cited

U.S. PATENT DOCUMENTS

| | | | |
|---|---|---|---|
| 4,444,879 A | 4/1984 | Foster et al. | |
| 5,681,699 A | 10/1997 | Rotter et al. | |
| 5,691,151 A | 11/1997 | Braun et al. | |
| 5,874,233 A | 2/1999 | Targan et al. | |
| 5,916,748 A | 6/1999 | Targan et al. | |
| 5,932,429 A | 8/1999 | Targan et al. | |
| 5,968,741 A | 10/1999 | Plevy et al. | |
| 6,033,864 A | 3/2000 | Braun et al. | |
| 6,218,129 B1 | 4/2001 | Walsh et al. | |
| 7,993,865 B2 | 8/2011 | Targan et al. | |
| 7,993,866 B2 | 8/2011 | Targan et al. | |
| 7,993,867 B2 | 8/2011 | Targan et al. | |

OTHER PUBLICATIONS

Teng et al. (Infection and Immunity 2006 vol. 74, p. 5609-5616).*
Rolhion et al. J. Bacteriology 2005 vol. 187, p. 2286-2296.*

* cited by examiner

*Primary Examiner* — Jacob Cheu
(74) *Attorney, Agent, or Firm* — Kilpatrick Townsend & Stockton LLP

(57) ABSTRACT

The present invention provides devices and methods for aiding in the diagnosis of Crohn's disease. The devices and methods accurately identify whether a sample from an individual is associated with inflammatory bowel disease (IBD) or a clinical subtype thereof such as Crohn's disease (CD). The present invention is useful for determining whether a sample from an individual is an IBD sample, or differentiating between CD and ulcerative colitis (UC). Thus, the present invention provides an accurate diagnostic prediction of IBD or a clinical subtype thereof and prognostic information useful for guiding treatment decisions.

18 Claims, 4 Drawing Sheets

ASSAYS AND METHODS FOR THE DETECTION OF CROHN'S DISEASE

CROSS-REFERENCE TO RELATED APPLICATIONS

This application claims priority to U.S. Provisional Application No. 61/367,328, filed Jul. 23, 2010, the disclosure of which is hereby incorporated by reference in its entirety for all purposes.

BACKGROUND OF THE INVENTION

Inflammatory bowel disease (IBD), which occurs worldwide and afflicts millions of people, is the collective term used to describe three gastrointestinal disorders of unknown etiology: Crohn's disease (CD), ulcerative colitis (UC), and indeterminate colitis (IC). IBD, together with irritable bowel syndrome (IBS), will affect one-half of all Americans during their lifetime, at a cost of greater than $2.6 billion dollars for IBD and greater than $8 billion dollars for IBS. A primary determinant of these high medical costs is the difficulty of diagnosing digestive diseases. The cost of IBD and IBS is compounded by lost productivity, with people suffering from these disorders missing at least 8 more days of work annually than the national average.

Inflammatory bowel disease has many symptoms in common with irritable bowel syndrome, including abdominal pain, chronic diarrhea, weight loss, and cramping, making definitive diagnosis extremely difficult. Of the 5 million people suspected of suffering from IBD in the United States, only 1 million are diagnosed as having IBD. The difficulty in differentially diagnosing IBD and IBS hampers early and effective treatment of these diseases. Thus, there is a need for rapid and sensitive testing methods for definitively distinguishing IBD from IBS.

Although progress has been made in precisely diagnosing clinical subtypes of IBD, current methods for diagnosing an individual as having either Crohn's disease, ulcerative colitis, or indeterminate colitis are relatively costly and require labor-intensive clinical, radiographic, endoscopic, and/or histological techniques. These costly techniques may be justified for those individuals previously diagnosed with or strongly suggested to have IBD, but a less expensive and highly sensitive alternative would be advantageous for first determining if an individual even has IBD. For example, such a highly sensitive screening assay would provide physicians with an inexpensive means for rapidly distinguishing individuals with IBD from those having IBS, thereby facilitating earlier and more appropriate therapeutic intervention and minimizing uncertainty for patients and their families. The highly sensitive screening assay could also be used to differentiate between clinical subtypes of IBD or could be combined with a subsequent, highly specific assay for determining if an individual diagnosed with IBD has either Crohn's disease, ulcerative colitis, or indeterminate colitis.

U.S. Pat. No. 7,138,237 to Targan et al. discloses methods and devices to determine the presence or absence of IgA anti-OmpC antibodies in a subject. IgA anti-OmpC antibodies are correlative to diagnosing Crohn's disease.

Despite the advantages of the technology disclosed and claimed in U.S. Pat. No. 7,138,237, there is a need for improved methods of diagnosing IBD at a very early stage of disease progression and for stratifying IBD into a clinical subtype such as Crohn's disease, ulcerative colitis, or indeterminate colitis. The present invention satisfies these needs and provides related advantages as well.

BRIEF SUMMARY OF THE INVENTION

The present invention provides devices and methods for aiding in the diagnosis of Crohn's disease. The devices and methods accurately classify or identify whether a sample from an individual is associated with inflammatory bowel disease (IBD) or a clinical subtype thereof such as Crohn's disease (CD). As a non-limiting example, the present invention is useful for determining whether a sample from an individual is an IBD sample, or differentiating between CD and ulcerative colitis (UC). Thus, the present invention provides an accurate diagnostic prediction of IBD or a clinical subtype thereof and prognostic information useful for guiding treatment decisions.

As such, in one embodiment, the present invention provides a diagnostic assay, the diagnostic assay comprising:
(a) determining the presence or absence of IgA anti-outer membrane protein A (anti-OmpA) antibodies in a sample by contacting the sample with an OmpA antigen or reactive fragment thereof, wherein the OmpA antigen is substantially-free of OmpC antigen, under conditions suitable to form a complex of the OmpA antigen or reactive fragment thereof and IgA anti-OmpA antibody;
(b) contacting the complex with a labeled indicator antibody to form a labeled complex; and
(c) detecting the presence or absence of the labeled complex with a detection device, wherein the presence of the labeled complex is associated with Crohn's disease.

In another embodiment, the present invention provides a diagnostic assay, the diagnostic assay comprising:
(a) obtaining a sample from a subject suspected of having inflammatory bowel disease;
(b) contacting the sample with an OmpA antigen or reactive fragment thereof, wherein the OmpA antigen is substantially-free of an OmpC antigen, under conditions suitable to form a complex of the OmpA antigen or reactive fragment thereof and IgA anti-OmpA antibody;
(c) contacting the complex with a labeled indicator antibody to form a labeled complex; and
(d) detecting the presence or absence of the labeled complex, and associating the presence of the IgA anti-OmpA antibodies in the sample with Crohn's disease.

In yet another embodiment, the present invention provides a diagnostic assay, the diagnostic assay comprising:
(a) contacting a sample from a subject suspected of having inflammatory bowel disease with an OmpA antigen or reactive fragment thereof, wherein the OmpA antigen is substantially-free of an OmpC antigen, under conditions suitable to form a complex of the OmpA antigen or reactive fragment thereof, and IgA anti-OmpA antibody, wherein the OmpA antigen comprises the amino acid sequence of SEQ ID NO: 1 or 90% identity thereof;
(b) contacting the complex with a labeled antibody to form a labeled complex;
(c) detecting the presence or absence of the labeled complex with a detection device; and
(d) associating the presence of the IgA anti-OmpA antibodies in the sample with Crohn's disease.

In still yet another embodiment, the present invention provides a diagnostic assay, the diagnostic assay comprising:
determining the presence of IgA anti-OmpA antibodies in the absence of IgA anti-OmpC antibodies, wherein the presence of the IgA anti-OmpA antibodies in the sample is associated with Crohn's disease.

In another embodiment, the present invention provides an ELISA assay method, the ELISA assay method comprising:
  determining the presence or absence of IgA anti-OmpA antibodies, wherein the IgA anti-OmpA antibodies are substantially-free of IgA anti-OmpC antibodies, using a labeled indicator antibody in an ELISA assay format and a detector; and
  associating the presence of the IgA anti-OmpA antibodies with Crohn's disease.

In still another embodiment, the present invention provides an assay system, the assay system comprising:
  (a) a plate comprising an OmpA antigen or reactive fragment thereof, wherein the OmpA antigen comprises the amino acid sequence of SEQ ID NO:1 or 90% identity thereof and is substantially-free of OmpC antigen;
  (b) an indicator secondary antibody specific for an OmpA autoantibody; and
  (c) instructions for detecting the presence or absence of a complex of the OmpA antigen, the OmpA autoantibody, and the indicator secondary antibody.

In another embodiment, the present invention provides an assay kit for improving the diagnosis of Crohn's disease comprising:
  (a) a plate well containing an OmpA antigen or reactive fragment thereof, wherein the OmpA antigen is substantially-free of OmpC antigen;
  (b) a labeled anti IgA antibody; and
  (c) instructions for detecting the presence or absence of IgA anti-OmpA antibodies in a patient's sample.

In still yet another embodiment, the present invention provides an assay kit to aid in the diagnosis of Crohn's disease comprising:
  (a) means for capturing IgA anti-OmpA antibodies, wherein the means is substantially-free of OmpC antigen; and
  (b) means for detecting the presence of the captured IgA anti-OmpA antibodies.

In another embodiment, the present invention provides an assay to aid in the detection of Crohn's disease comprising:
  (a) contacting a sample with an OmpA antigen or reactive fragment thereof, wherein the OmpA antigen is substantially-free of an OmpC antigen, under conditions suitable to transform the OmpA antigen into a complex comprising the OmpA antigen or reactive fragment thereof and IgA anti-OmpA antibody;
  (b) contacting the complex with a labeled indicator antibody to transform the complex into a labeled complex; and
  (c) detecting the presence of IgA anti-OmpA antibodies in the sample.

In still yet another embodiment, the present invention provides a method for performing an assay for improving the diagnosis of Crohn's disease, the method comprising:
  (a) detecting the presence of IgA anti-OmpA antibodies in a patient's sample, wherein the IgA anti-OmpA antibodies are substantially-free of IgA anti-OmpC antibodies; and
  (b) reporting the presence or absence of IgA anti-OmpA antibodies in the patient's sample to improve the diagnosis of Crohn's disease.

These and other aspects, embodiments and objects will become more apparent when read with the detailed description and figures that follow.

DETAILED DESCRIPTION OF THE INVENTION

I. Introduction

Figure 1:
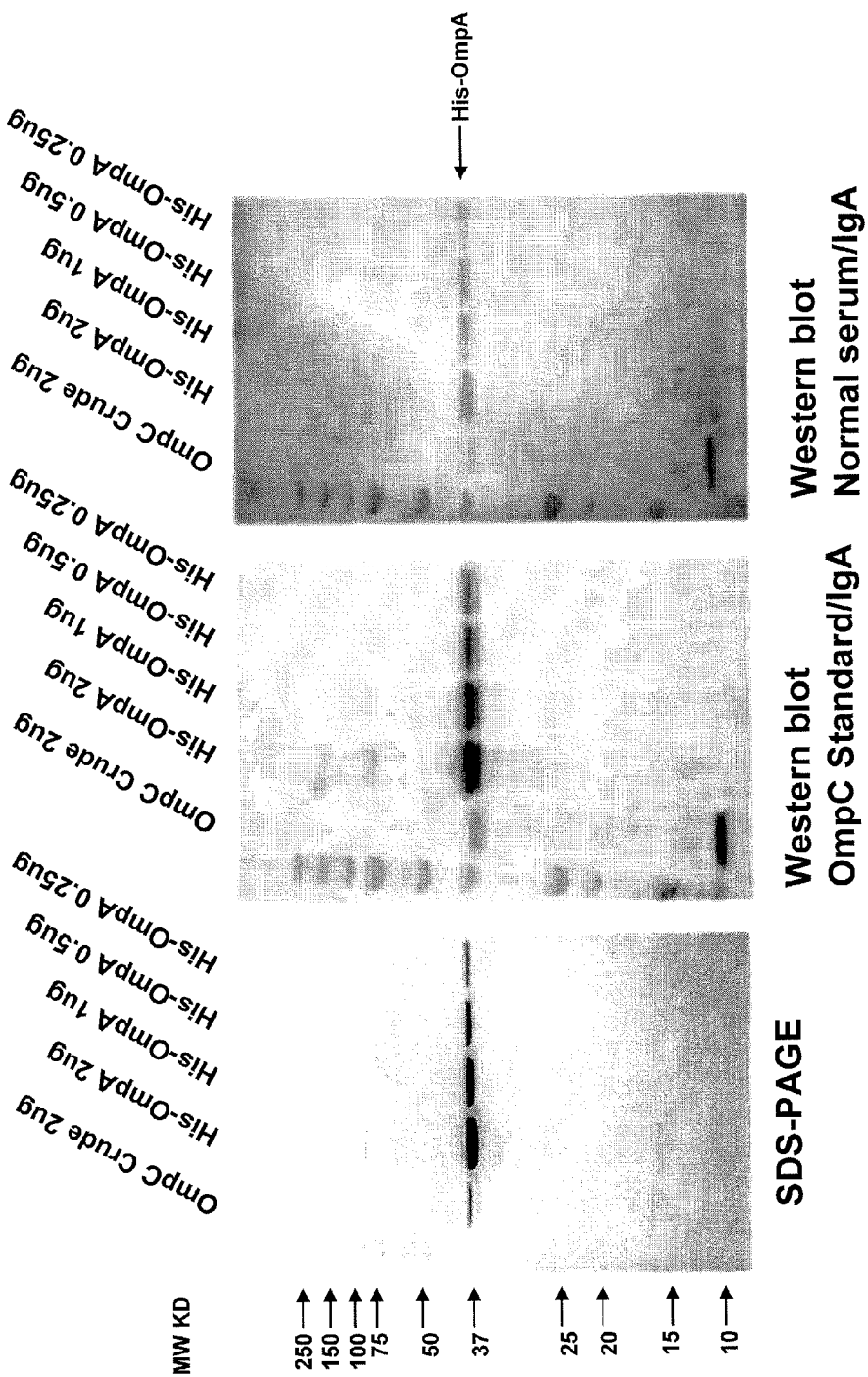
FIG. 1 illustrates an analysis of recombinant His-OmpA by SDS-PAGE and Western blotting. His-OmpA antigen was highly sensitive and immuno-reactive against IgA anti-OmpA antibodies in pooled Crohn's disease patient sera that were also positive for IgA anti-OmpC antibodies.

Diagnosing a patient as having inflammatory bowel disease (IBD) and especially Crohn's disease can be challenging due to the similarity in symptoms between IBD and other diseases or disorders. For example, patients who have irritable bowel syndrome (IBS), but who exhibit mild signs and symptoms such as bloating, diarrhea, constipation, and abdominal pain can be difficult to distinguish from patients with IBD. As a result, the similarity in symptoms between IBD and IBS renders rapid and accurate diagnosis difficult and hampers early and effective treatment of the disease. Advantageously, the present invention provides devices and methods for aiding in the diagnosis of IBD and especially Crohn's disease.

II. Definitions

As used herein, the following terms have the meanings ascribed to them unless specified otherwise.

The term "classifying" includes "to identify" "to associate" or "to categorize" a sample with a disease state. In certain instances, "classifying" is based on statistical evidence, empirical evidence, or both. In certain embodiments, the devices and methods of classifying use a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "inflammatory bowel disease" or "IBD" refers to gastrointestinal disorders including, without limitation, Crohn's disease (CD), ulcerative colitis (UC), and indeterminate colitis (IC). Inflammatory bowel diseases such as CD, UC, and IC are distinguished from all other disorders, syndromes, and abnormalities of the gastroenterological tract, including irritable bowel syndrome (IBS).

The term "sample" includes any biological specimen obtained from an individual. Suitable samples for use in the present invention include, without limitation, whole blood, plasma, serum, saliva, urine, stool, tears, any other bodily fluid, tissue samples (e.g., biopsy), and cellular extracts thereof (e.g., red blood cellular extract). In a preferred embodiment, the sample is a serum sample. The use of samples such as serum, saliva, and urine is well known in the art (see, e.g., Hashida et al., *J. Clin. Lab. Anal.*, 11:267-86 (1997)). One skilled in the art will appreciate that samples such as serum samples can be diluted prior to the analysis of marker levels.

The term "marker" includes any biochemical marker, serological marker, genetic marker, or other clinical or echographic characteristic that can be used to classify a sample from an individual as an IBD (e.g., CD or UC) sample. Non-limiting examples of markers suitable for use in the present invention are described below and include anti-neutrophil antibodies (e.g., ANCA, pANCA, cANCA, NSNA, SAPPA, etc.), anti-*Saccharomyces cerevisiae* antibodies (e.g., ASCA-IgA, ASCA-IgG, ASCA-IgM, etc.), antimicrobial antibodies (e.g., anti-OmpA antibodies, anti-OmpC antibodies, anti-flagellin antibodies, anti-I2 antibodies, etc.), lactoferrin, anti-lactoferrin antibodies, elastase, C-reactive protein (CRP), calprotectin, hemoglobin, NOD2/CARD15, and combinations thereof. One skilled in the art will know of additional markers suitable for use in the present invention.

The term "individual," "subject," or "patient" typically refers to humans, but also to other animals including, e.g., other primates, rodents, canines, felines, equines, ovines, porcines, and the like.

As used herein, the term "substantially the same amino acid sequence" includes an amino acid sequence that is similar, but not identical to, the naturally-occurring amino acid sequence. For example, an amino acid sequence, i.e., polypeptide, that has substantially the same amino acid sequence as the OmpA protein in SEQ ID NO: 1 can have one or more modifications such as amino acid additions, deletions, or substitutions relative to the amino acid sequence of the naturally-occurring OmpA protein, provided that the modified polypeptide retains substantially at least one biological activity of OmpA such as immunoreactivity. Comparison for substantial similarity between amino acid sequences is usually performed with sequences between about 6 and 100 residues, preferably between about 10 and 100 residues, and more preferably between about 25 and 35 residues. A particularly useful modification of a polypeptide of the present invention, or a fragment thereof, is a modification that confers, for example, increased stability or reactivity. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

As used herein, the term "OmpA antigen" or "OmpA" includes a protein that has at least about 50% amino acid identity with *E. coli* OmpA (SEQ ID NO:1). As a non-limiting example, an OmpA antigen of the invention can have at least about 60%, 65%, 70%, 75%, 80%, 85%, 90%, 91%, 92%, 93%, 94%, 95%, 96%, 97%, 98%, or 99% amino acid identity with *E. coli* OmpA (SEQ ID NO:1). For use in the methods of the invention, an OmpA antigen can be partially purified, for example, by spheroplast lysis from OmpA, or can be similarly prepared from a variety of other *E. coli* strains, which can contain OmpA. An OmpA antigen also can be prepared recombinantly by expressing an encoding nucleic acid sequence such as that available as GenBank accession V00307.1 using methods well known in the art (see, for example, Ausubel et al., Current Protocols in Molecular Biology John Wiley & Sons, Inc. New York (1999)).

As used herein, the term "fragment" includes a peptide, polypeptide or protein segment of at least about 10, 15, 20, 25, 30, 40, 50, 60, 70, 80, 90, 100, 125, 130, 150, 160, 180, 200, 210, 225, 230, 250, 260, 275, 280, or 300 amino acids of the full-length SEQ ID NO: 1, provided that the fragment retains preferential reactivity with IgA antibodies in sera of Crohn's disease patients, e.g., the OmpA fragment is immunoreactive with IgA anti-OmpA antibodies. In certain instances, the fragment is between about 30-100, or about 125-200, or about 225-250 amino acids in length. In other instances, the fragment is the immunogenic epitaph of SEQ ID NO:1. An ELISA using OmpA protein or a fragment thereof is useful for determining whether a sample is positive for anti-OmpA antibodies, or for determining anti-OmpA antibody levels in a sample. In some embodiments, the OmpA antigen or fragment thereof comprises a tag such as a polyhistidine tag (e.g., 6×His (SEQ ID NO:4) tag) at the amino-terminus and/or carboxyl-terminus.

As used herein, the term "substantially-free of" includes a meaning that one antigen (e.g., OmpA) is devoid or free of another antigen (e.g., OmpC). For example, in an ELISA assay, if recombinant OmpA is plated, the plate is substantially-free of interfering proteins such as OmpC. In certain instances, substantially-free means that the protein being plated is free of contaminating proteins, or that contaminating proteins will not interfere with the measurement. The contaminants are typically less than 10% of the total protein being plated, or less than 5%, or less than 4%, or less than 3%, or less than 2%, or less than 1%, or less than 0.9%, or less than 0.5%, or less than 0.1%, or less than 0.01%, or less than 0.001% of the total protein being plated.

The term "prognosis" includes a prediction of the probable course and outcome of IBD or the likelihood of recovery from the disease. In some embodiments, the use of statistical algorithms provides a prognosis of IBD in an individual. For example, the prognosis can be surgery, development of a clinical subtype of IBD (e.g., CD or UC), development of one or more clinical factors, development of intestinal cancer, or recovery from the disease.

The term "diagnosing IBD" includes the use of the devices, methods, and systems, of the present invention to determine the presence or absence of IBD in an individual. The term also includes devices, methods, and systems for assessing the level of disease activity in an individual. In some embodiments, statistical algorithms are used to diagnose a mild, moderate, severe, or fulminant form of IBD based upon the criteria developed by Truelove et al., *Br. Med. J.*, 12:1041-1048 (1955). In other embodiments, statistical algorithms are used to diagnose a mild to moderate, moderate to severe, or severe to fulminant form of IBD based upon the criteria developed by Hanauer et al., *Am. J. Gastroenterol.*, 92:559-566 (1997). In other embodiments, the presence of OmpA antibodies is used to diagnose Crohn's disease. One skilled in the art will know of other methods for evaluating the severity of IBD in an individual.

The term "monitoring the progression or regression of IBD" includes the use of the devices, methods, and systems of the present invention to determine the disease state (e.g., presence or severity of IBD) of an individual. In certain instances, the results of a statistical algorithm (e.g., a learning statistical classifier system) are compared to those results obtained for the same individual at an earlier time. In some aspects, the devices, methods, and systems of the present invention can also be used to predict the progression of IBD, e.g., by determining a likelihood for IBD to progress either rapidly or slowly in an individual based on the presence or level of at least one marker in a sample. In other aspects, the devices, methods, and systems of the present invention can also be used to predict the regression of IBD, e.g., by determining a likelihood for IBD to regress either rapidly or slowly in an individual based on the presence or level of at least one marker in a sample.

The term "monitoring drug efficacy in an individual receiving a drug useful for treating IBD" includes the use of the devices, methods, and systems of the present invention to determine the disease state (e.g., presence or severity of IBD) of an individual after a therapeutic agent for treating IBD has been administered. In certain instances, the results of a statistical algorithm (e.g., a learning statistical classifier system) are compared to those results obtained for the same individual before initiation of use of the therapeutic agent or at an earlier time in therapy. As used herein, a drug useful for treating IBD is any compound or drug used to improve the health of the individual and includes, without limitation, IBD drugs such as aminosalicylates (e.g., mesalazine, sulfasalazine, and the like), corticosteroids (e.g., prednisone), thiopurines (e.g., azathioprine, 6-mercaptopurine, and the like), methotrexate, monoclonal antibodies (e.g., infliximab), free bases thereof, pharmaceutically acceptable salts thereof, derivatives thereof, analogs thereof, and combinations thereof.

The term "optimizing therapy in an individual having IBD" includes the use of the devices, methods and systems of the present invention to determine the course of therapy for an individual before a therapeutic agent (e.g., IBD drug) has been administered or to adjust the course of therapy for an individual after a therapeutic agent has been administered in order to optimize the therapeutic efficacy of the therapeutic agent. In certain instances, the results of a statistical algorithm (e.g., a learning statistical classifier system) are compared to those results obtained for the same individual at an earlier time during the course of therapy. As such, a comparison of the results provides an indication for the need to change the course of therapy or an indication for the need to increase or decrease the dose of the current course of therapy.

The term "course of therapy" includes any therapeutic approach taken to relieve or prevent one or more symptoms (i.e., clinical factors) associated with IBD. The term encompasses administering any compound, drug, procedure, or regimen useful for improving the health of an individual with IBD and includes any of the therapeutic agents (e.g., IBD drugs) described above as well as surgery. One skilled in the art will appreciate that either the course of therapy or the dose of the current course of therapy can be changed, e.g., based upon the results of a statistical algorithm (e.g., a learning statistical classifier system) obtained using the devices, methods and systems of the present invention.

The term "therapeutically effective amount or dose" includes a dose of a drug that is capable of achieving a therapeutic effect in a subject in need thereof. For example, a therapeutically effective amount of a drug useful for treating IBD can be the amount that is capable of preventing or relieving one or more symptoms associated with IBD. The exact amount can be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "sensitivity" refers to the probability that a diagnostic device, method, and system of the present invention gives a positive result when the sample is positive, e.g., having IBD or a clinical subtype thereof. Sensitivity is calculated as the number of true positive results divided by the sum of the true positives and false negatives. Sensitivity essentially is a measure of how well a device, method, or system, of the present invention correctly identifies those with IBD or a clinical subtype thereof from those without the disease. The device, method, system, or statistical algorithms can be selected such that the sensitivity of classifying IBD or a clinical subtype thereof (e.g., CD or UC) is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "specificity" refers to the probability that a diagnostic device, methods, and system of the present invention gives a negative result when the sample is not positive, e.g., not having IBD or a clinical subtype thereof. Specificity is calculated as the number of true negative results divided by the sum of the true negatives and false positives. Specificity essentially is a measure of how well a device, method, or system of the present invention excludes those who do not have IBD or a clinical subtype thereof from those who have the disease. The device, method, system, or statistical algorithms can be selected such that the specificity of classifying IBD or a clinical subtype thereof (e.g., CD or UC) is at least about 70%, for example, at least about 75%, 80%, 85%, 86%, 87%, 88%, 89%, 90%, 91%, 92%, 93%, 94%, 95%, 96%, 97%, 98%, or 99%.

As used herein, the term "negative predictive value" or "NPV" refers to the probability that an individual identified as not having IBD or a clinical subtype thereof actually does not have the disease. Negative predictive value can be calculated as the number of true negatives divided by the sum of the true negatives and false negatives. Negative predictive value is determined by the characteristics of the diagnostic device, method, or system as well as the prevalence of the disease in the population analyzed. The statistical algorithms can be selected such that the negative predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "positive predictive value" or "PPV" refers to the probability that an individual identified as having IBD or a clinical subtype thereof actually has the disease. Positive predictive value can be calculated as the number of true positives divided by the sum of the true positives and false positives. Positive predictive value is determined by the characteristics of the diagnostic device, method, or system as well as the prevalence of the disease in the population analyzed. The statistical algorithms can be selected such that the positive predictive value in a population having a disease prevalence is in the range of about 80% to about 99% and can be, for example, at least about 80%, 85%, 86%, 87%, 88%, 89%, 90%, 91%, 92%, 93%, 94%, 95%, 96%, 97%, 98%, or 99%.

Predictive values, including negative and positive predictive values, are influenced by the prevalence of the disease in the population analyzed. In the devices, methods and systems of the present invention, the statistical algorithms can be selected to produce a desired clinical parameter for a clinical population with a particular IBD prevalence. For example, learning statistical classifier systems can be selected for an IBD prevalence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%, which can be seen, e.g., in a clinician's office such as a gastroenterologist's office or a general practitioner's office.

As used herein, the term "overall agreement" or "overall accuracy" refers to the accuracy with which a device, method, or system of the present invention classifies a disease state. Overall accuracy is calculated as the sum of the true positives and true negatives divided by the total number of sample results and is affected by the prevalence of the disease in the population analyzed. For example, the statistical algorithms can be selected such that the overall accuracy in a patient population having a disease prevalence is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The sample used for detecting or determining the presence or level of anti-OmpA antibodies or at least one marker is typically whole blood, plasma, serum, saliva, urine, stool (i.e., feces), tears, and any other bodily fluid, or a tissue sample (i.e., biopsy) such as a small intestine or colon sample. Preferably, the sample is serum, whole blood, plasma, stool, urine, or a tissue biopsy. In certain instances, the method of the present invention further comprises obtaining the sample from the individual prior to detecting or determining the presence or level of at least one marker in the sample.

In some embodiments, the method of the present invention comprises determining the presence or level of anti-OmpA antibody together with ANCA, ASCA-IgA, ASCA-IgG, anti-OmpC antibody, anti-flagellin antibody, and pANCA in a sample such as serum, plasma, whole blood, or stool. A panel consisting of one or more of the IBD markers described herein may be constructed and used for determining the presence or severity of IBD (e.g., CD or UC) in the individual.

In certain instances, the presence or level of anti-OmpA antibodies or at least one marker is determined using an immunoassay or an immunohistochemical assay. A non-limiting example of an immunoassay suitable for use in the method of the present invention includes an ELISA. Examples of immunohistochemical assays suitable for use in the method of the present invention include, but are not limited to, immunofluorescence assays such as direct fluorescent antibody assays, IFA assays, anticomplement immunofluorescence assays, and avidin-biotin immunofluorescence assays. Other types of immunohistochemical assays include immunoperoxidase assays.

III. Embodiments

The present invention provides diagnostic devices, methods or systems for diagnosing or aiding in the diagnosis of IBD and especially Crohn's disease based on the presence or absence of IgA antibodies to outer membrane protein A ("anti-OmpA"). In contrast to the normal individuals, significant IgA OmpA reactivity is present in sera from patients having Crohn's disease. The results presented herein indicate that IgA OmpA reactivity can be valuable in increasing the number of Crohn's disease patients that are diagnosed with the disease, thereby facilitating earlier and more appropriate treatment.

In general, a "porin" is a class of transmembrane proteins that are found in the outer membranes of bacteria, including gram-negative enteric bacteria such as *E. coli*. The porins in the outer membrane of an *E. coli* cell provide channels for passage of disaccharides, phosphate and similar molecules. Porins can be trimers of identical subunits arranged to form a barrel-shaped structure with a pore at the center (Lodish et al., Molecular Cell Biology, Chapter 14 (1995)).

Outer membrane protein A ("OmpA") is a major protein in the *Escherichia coli* outer membrane. OmpA is a major target in mammalian host cell defense and plays a vital structural role in *E. coli*, with the β-barrel structure of OmpA being important for outer membrane stability. It has been proposed that OmpA is composed of three functional domains including a hydrophilic extracellular mass, a β-barrel transmembrane structure, and a peptidoglycan binding domain (see, Y. Wang et al., *Biochemical and Biophysical Research Communications*, Volume 292, Issue 2, 29 Mar. 2002, Pages 396-401).

The outer-membrane protein C ("OmpC") is one of the major porin proteins found in the outer membranes of bacteria such as *E. coli*. OmpC is similar in structure and function to outer-membrane protein F ("OmpF"). Both assemble as trimers in the outer membrane to form aqueous channels that allow the passive diffusion of small, hydrophilic molecules across the hydrophobic barrier. However, OmpC pores have a diameter of 1.1 nm, while OmpF pores have a diameter of 1.2 nm. This difference results in a slower rate of diffusion through the OmpC pores than through the OmpF pores.

Porin expression can be influenced by environmental conditions, including osmolarity, temperature, growth phase and toxin concentration. For example, in the intestine, where both nutrient and toxic molecule concentrations are relatively high, OmpC, with a smaller pore diameter, is the predominant porin (Pratt et al., *Mol. Micro.*, 20:911 917 (1996)).

As used herein, the term "OmpA antigen" or "OmpA" means a protein that has linear or conformational homology to OmpA. An OmpA antigen can be derived from a gram-negative bacterium, such as *E. coli*, and can be a species homolog of *E. coli* OmpA (SEQ ID NO:1). In nature, an OmpA antigen is a protein that is important to the outer membrane of bacteria which allows the passage of small molecules, or a precursor of such a protein.

As used herein, the term "OmpC antigen" or "OmpC" means a protein that has linear or conformational homology to OmpC. A OmpC antigen can be derived from a gram-negative bacterium, such as *E. coli*, and can be a species homolog of *E. coli* OmpC (SEQ ID NO:2 or SEQ ID NO:3). In nature, an OmpC antigen is a protein that forms a trimeric structure in the outer membrane of bacteria which allows the passage of small molecules, or a precursor of such a protein.

In one embodiment, the present invention provides a diagnostic assay, comprising:

determining the presence of IgA anti-OmpA antibodies in the absence of IgA anti-OmpC antibodies, wherein the presence of the IgA anti-OmpA antibodies in the sample is associated with Crohn's disease.

In certain aspects, the IgA anti-OmpA antibodies are determined or the concentration measured without interfering antibodies. In other words, it is important to measure the anti-OmpA antibodies without other contaminating proteins such as other porins or other outer membrane porins. In preferred embodiments of the invention, IgA anti-OmpA antibodies are determined or the concentration measured in the absence of IgA anti-OmpC antibodies.

It is known, for example, that IgA anti-OmpC antibodies are present in Crohn's Disease samples about 52% of the time (see, U.S. Pat. No. 7,138,237). By eliminating or ensuring detection of only OmpA antibodies substantially-free of other anti-porin antibodies, such as anti-OmpC antibodies, it is then possible to determine the presence of IgA anti-OmpA antibodies in the absence of IgA anti-OmpC antibodies. In one preferred embodiment, an immunoassay such as an enzyme-linked immunosorbent assay (ELISA) is used in which recombinant OmpA is used as an antigen. In this manner, the presence of IgA anti-OmpA antibodies is determined.

In certain embodiments, measuring, detecting or determining IgA anti-OmpA antibodies from a sample suspected of being an IBD or CD sample involves an ELISA technique wherein a recombinant OmpA antigen is immobilized on a solid support (e.g., a polystyrene microtiter plate) either non-specifically (via adsorption to the surface) or specifically. After the OmpA antigen is immobilized, the sample suspected of containing an IgA anti-OmpA antibody is added, forming a complex with the OmpA antigen, if present. A second antibody, referred to as "the detection antibody," "secondary antibody," or "labeled indicator antibody" can then be used to detect anti-OmpA antibodies complexed to the plated antigen. The detection antibody can be covalently linked to an enzyme, chromophore or fluorophore through bioconjugation. The detection antibody has affinity for the bound complex. Between each step, the plate is typically washed with a detergent solution to remove any proteins or antibodies that are not specifically bound. After the final wash step, the plate is developed by adding an enzymatic substrate to produce a visible signal, or read by a plate reading device (e.g., spectrophotometer) which indicates the quantity of antibodies in the sample. The amount of anti-OmpA antibodies can be compared to a standard curve.

The ELISA typically involves chromogenic reporters and substrates that produce some kind of observable color change to indicate the presence of antigen or analyte. Alternatively, ELISA-like techniques can be used which involve fluorogenic, electrochemiluminescent, and real-time PCR reporters to create quantifiable signals. These reporters can have various advantages including higher sensitivities and multiplexing than using a complexed enzyme.

In one embodiment, the present invention provides a diagnostic assay comprising:
(a) determining the presence or absence of IgA anti-outer membrane protein A (anti-OmpA) antibodies in a sample by contacting the sample with an OmpA antigen or reactive fragment thereof, wherein the OmpA antigen is substantially-free of OmpC antigen, under conditions suitable to form a complex of the OmpA antigen or reactive fragment thereof and IgA anti-OmpA antibody;
(b) contacting the complex with a labeled indicator antibody to form a labeled complex; and
(c) detecting the presence or absence of the labeled complex with a detection device, wherein the presence of the labeled complex is associated with Crohn's disease.

In one preferred embodiment, an OmpA antigen which is substantially-free of OmpC antigen is accomplished by using recombinant techniques. In certain other embodiments, OmpA protein can be purified using conventional methods known to those in the protein purification field. In this manner, the amount of contaminating protein is insubstantial, or the amount of OmpC is an insubstantial amount (a de minimus amount, i.e., a non-interfering amount). In certain other embodiments, it is possible to use an *E coli* strain that is OmpC deficient or an OmpC deficient mutant to prepare OmpA antigen.

In another embodiment, the present invention provides a diagnostic assay, the diagnostic assay comprising:
(a) obtaining a sample from a subject suspected of having inflammatory bowel disease;
(b) contacting the sample with an OmpA antigen or reactive fragment thereof, wherein the OmpA antigen is substantially-free of an OmpC antigen, under conditions suitable to form a complex of the OmpA antigen or reactive fragment thereof and IgA anti-OmpA antibody;
(c) contacting the complex with a labeled indicator antibody to form a labeled complex; and
(d) detecting the presence or absence of the labeled complex, and associating the presence of the IgA anti-OmpA antibodies in the sample with Crohn's disease.

In certain instances, the labeled indicator antibody or detection antibody forms a labeled complex. The labeled complex can be detected using a detection device such as a spectrophotometer, a plate reader or fluorometer.

In certain instances, the ratio of concentration levels of anti-OmpA to anti-OmpC antibodies is indicative to the diagnosis and/or prognosis of Crohn's Disease.

IV. Clinical Subtypes of IBD

Crohn's disease (CD) is a disease of chronic inflammation that can involve any part of the gastrointestinal tract. Commonly, the distal portion of the small intestine, i.e., the ileum, and the cecum are affected. In other cases, the disease is confined to the small intestine, colon, or anorectal region. CD occasionally involves the duodenum and stomach, and more rarely the esophagus and oral cavity.

The variable clinical manifestations of CD are, in part, a result of the varying anatomic localization of the disease. The most frequent symptoms of CD are abdominal pain, diarrhea, and recurrent fever. CD is commonly associated with intestinal obstruction or fistula, an abnormal passage between diseased loops of bowel. CD also includes complications such as inflammation of the eye, joints, and skin, liver disease, kidney stones, and amyloidosis. In addition, CD is associated with an increased risk of intestinal cancer.

Several features are characteristic of the pathology of CD. The inflammation associated with CD, known as transmural inflammation, involves all layers of the bowel wall. Thickening and edema, for example, typically also appear throughout the bowel wall, with fibrosis present in long-standing forms of the disease. The inflammation characteristic of CD is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of CD is the presence of discrete aggregations of inflammatory cells, known as granulomas, which are generally found in the submucosa. Some CD cases display typical discrete granulomas, while others show a diffuse granulomatous reaction or a nonspecific transmural inflammation. As a result, the presence of discrete granulomas is indicative of CD, although the absence of granulomas is also consistent with the disease. Thus, transmural or discontinuous inflammation, rather than the presence of granulomas, is a preferred diagnostic indicator of CD (Rubin and Farber, Pathology (Second Edition), Philadelphia, J. B. Lippincott Company (1994)).

Ulcerative colitis (UC) is a disease of the large intestine characterized by chronic diarrhea with cramping, abdominal pain, rectal bleeding, loose discharges of blood, pus, and mucus. The manifestations of UC vary widely. A pattern of exacerbations and remissions typifies the clinical course for about 70% of UC patients, although continuous symptoms without remission are present in some patients with UC. Local and systemic complications of UC include arthritis, eye inflammation such as uveitis, skin ulcers, and liver disease. In addition, UC, and especially the long-standing, extensive form of the disease is associated with an increased risk of colon carcinoma.

UC is a diffuse disease that usually extends from the most distal part of the rectum for a variable distance proximally. The term "left-sided colitis" describes an inflammation that involves the distal portion of the colon, extending as far as the splenic flexure. Sparing of the rectum or involvement of the right side (proximal portion) of the colon alone is unusual in UC. The inflammatory process of UC is limited to the colon and does not involve, for example, the small intestine, stomach, or esophagus. In addition, UC is distinguished by a superficial inflammation of the mucosa that generally spares the deeper layers of the bowel wall. Crypt abscesses, in which degenerated intestinal crypts are filled with neutrophils, are also typical of UC (Rubin and Farber, supra).

In comparison with CD, which is a patchy disease with frequent sparing of the rectum, UC is characterized by a continuous inflammation of the colon that usually is more severe distally than proximally. The inflammation in UC is superficial in that it is usually limited to the mucosal layer and is characterized by an acute inflammatory infiltrate with neutrophils and crypt abscesses. In contrast, CD affects the entire thickness of the bowel wall with granulomas often, although not always, present. Disease that terminates at the ileocecal valve, or in the colon distal to it, is indicative of UC, while involvement of the terminal ileum, a cobblestone-like appearance, discrete ulcers, or fistulas suggests CD.

Indeterminate colitis (IC) is a clinical subtype of IBD that includes both features of CD and UC. Such an overlap in the symptoms of both diseases can occur temporarily (e.g., in the early stages of the disease) or persistently (e.g., throughout the progression of the disease) in patients with IC. Clinically, IC is characterized by abdominal pain and diarrhea with or without rectal bleeding. For example, colitis with intermittent multiple ulcerations separated by normal mucosa is found in patients with the disease. Histologically, there is a pattern of severe ulceration with transmural inflammation. The rectum is typically free of the disease and the lymphoid inflammatory cells do not show aggregation. Although deep slit-like fissures are observed with foci of myocytolysis, the intervening mucosa is typically minimally congested with the preservation of goblet cells in patients with IC.

V. IBD Markers

In certain embodiments, the present invention provides methods of diagnosing IBD or clinical subtypes thereof using anti-OmpA as well as other markers. A variety of inflammatory bowel disease (IBD) markers, such as biochemical markers, serological markers, genetic markers, or other clinical or echographic characteristics, are suitable for use and can be combined with statistical algorithms to classify a sample from an individual as an IBD sample. The IBD markers described herein are also suitable for use with anti-OmpA and with statistical algorithms for differentiating between clinical subtypes of IBD, e.g., by classifying a sample from an individual as a CD or UC sample. Examples of markers suitable for use in the present invention include, but are not limited to, anti-neutrophil antibodies (e.g., ANCA, pANCA, cANCA, NSNA, SAPPA, etc.), anti-*Saccharomyces cerevisiae* antibodies (e.g., ASCA-IgA, ASCA-IgG, ASCA-IgM, etc.), anti-microbial antibodies (e.g., anti-OmpC antibodies, anti-flagellin antibodies, anti-I2 antibodies, etc.), lactoferrin, anti-lactoferrin antibodies, elastase, C-reactive protein (CRP), calprotectin, hemoglobin, NOD2/CARD15, and combinations thereof. One skilled in the art will know of additional markers suitable for use in the statistical algorithms of the present invention.

The determination of ANCA levels and/or the presence or absence of pANCA in a sample is useful in the present invention. As used herein, the term "anti-neutrophil cytoplasmic antibody" or "ANCA" includes antibodies directed to cytoplasmic and/or nuclear components of neutrophils. ANCA activity can be divided into several broad categories based upon the ANCA staining pattern in neutrophils: (1) cytoplasmic neutrophil staining without perinuclear highlighting (cANCA); (2) perinuclear staining around the outside edge of the nucleus (pANCA); (3) perinuclear staining around the inside edge of the nucleus (NSNA); and (4) diffuse staining with speckling across the entire neutrophil (SAPPA). In certain instances, pANCA staining is sensitive to DNase treatment. The term ANCA encompasses all varieties of anti-neutrophil reactivity, including, but not limited to, cANCA, pANCA, NSNA, and SAPPA. Similarly, the term ANCA encompasses all immunoglobulin isotypes including, without limitation, immunoglobulin A and G.

ANCA levels in a sample from an individual can be determined, for example, using an immunoassay such as an enzyme-linked immunosorbent assay (ELISA) with alcohol-fixed neutrophils. The presence or absence of a particular category of ANCA such as pANCA can be determined, for example, using an immunohistochemical assay such as an indirect fluorescent antibody (IFA) assay. Preferably, the presence or absence of pANCA in a sample is determined using an immunofluorescence assay with DNase-treated, fixed neutrophils. In addition to fixed neutrophils, antigens specific for ANCA that are suitable for determining ANCA levels include, without limitation, unpurified or partially purified neutrophil extracts; purified proteins, protein fragments, or synthetic peptides such as histone H1 or ANCA-reactive fragments thereof (see, e.g., U.S. Pat. No. 6,074,835); histone H1-like antigens, porin antigens, Bacteroides antigens, or ANCA-reactive fragments thereof (see, e.g., U.S. Pat. No. 6,033,864); secretory vesicle antigens or ANCA-reactive fragments thereof (see, e.g., U.S. patent application Ser. No. 08/804,106); and anti-ANCA idiotypic antibodies. One skilled in the art will appreciate that the use of additional antigens specific for ANCA is within the scope of the present invention.

The determination of ASCA (e.g., ASCA-IgA and/or ASCA-IgG) levels in a sample is also useful in the present invention. As used herein, the term "anti-*Saccharomyces cerevisiae* immunoglobulin A" or "ASCA-IgA" includes antibodies of the immunoglobulin A isotype that react specifically with *S. cerevisiae*. Similarly, the term "anti-*Saccharomyces cerevisiae* immunoglobulin G" or "ASCA-IgG" includes antibodies of the immunoglobulin G isotype that react specifically with *S. cerevisiae*.

The determination of whether a sample is positive for ASCA-IgA or ASCA-IgG is made using an antigen specific for ASCA. Such an antigen can be any antigen or mixture of antigens that is bound specifically by ASCA-IgA and/or ASCA-IgG. Although ASCA antibodies were initially characterized by their ability to bind *S. cerevisiae*, those of skill in the art will understand that an antigen that is bound specifically by ASCA can be obtained from *S. cerevisiae* or from a variety of other sources so long as the antigen is capable of binding specifically to ASCA antibodies. Accordingly, exemplary sources of an antigen specific for ASCA, which can be used to determine the levels of ASCA-IgA and/or ASCA-IgG in a sample, include, without limitation, whole killed yeast cells such as *Saccharomyces* or *Candida* cells; yeast cell wall mannan such as phosphopeptidomannan (PPM); oligosaccharides such as oligomannosides; neoglycolipids; anti-ASCA idiotypic antibodies; and the like. Different species and strains of yeast, such as *S. cerevisiae* strain Su1, Su2, CBS 1315, or BM 156, or *Candida albicans* strain VW32, are suitable for use as an antigen specific for ASCA-IgA and/or ASCA-IgG. Purified and synthetic antigens specific for ASCA are also suitable for use in determining the levels of ASCA-IgA and/or ASCA-IgG in a sample. Examples of purified antigens include, without limitation, purified oligosaccharide antigens such as oligomannosides. Examples of synthetic antigens include, without limitation, synthetic oligomannosides such as those described in U.S. Patent Publication No. 20030105060, e.g., D-Man β(1-2) D-Manβ(1-2) D-Man β(1-2) D-Man-OR, D-Man α(1-2) D-Man α(1-2) D-Man α(1-2) D-Man-OR, and D-Man α(1-3) D-Man α(1-2) D-Man α(1-2) D-Man-OR, wherein R is a hydrogen atom, a $C_1$ to $C_{20}$ alkyl, or an optionally labeled connector group.

Preparations of yeast cell wall mannans, e.g., PPM, can be used in determining the levels of ASCA-IgA and/or ASCA-IgG in a sample. Such water-soluble surface antigens can be prepared by any appropriate extraction technique known in the art, including, for example, by autoclaving, or can be obtained commercially (see, e.g., Lindberg et al., *Gut*, 33:909-913 (1992)). The acid-stable fraction of PPM is also useful in the statistical algorithms of the present invention (Sendid et al., *Clin. Diag. Lab. Immunol.*, 3:219-226 (1996)). An exemplary PPM that is useful in determining ASCA levels in a sample is derived from *S. uvarum* strain ATCC #38926.

Purified oligosaccharide antigens such as oligomannosides can also be useful in determining the levels of ASCA-IgA and/or ASCA-IgG in a sample. The purified oligomannoside antigens are preferably converted into neoglycolipids as described in, for example, Faille et al., *Eur. J. Microbiol. Infect. Dis.*, 11:438-446 (1992). One skilled in the art understands that the reactivity of such an oligomannoside antigen with ASCA can be optimized by varying the mannosyl chain length (Frosh et al., *Proc Natl. Acad. Sci. USA*, 82:1194-1198 (1985)); the anomeric configuration (Fukazawa et al., In "Immunology of Fungal Disease," E. Kurstak (ed.), Marcel Dekker Inc., New York, pp. 37-62 (1989); Nishikawa et al., *Microbiol. Immunol.*, 34:825-840 (1990); Poulain et al., *Eur. J. Clin. Microbiol.*, 23:46-52 (1993); Shibata et al., *Arch. Biochem. Biophys.*, 243:338-348 (1985); Trinel et al., *Infect. Immun.*, 60:3845-3851 (1992)); or the position of the linkage (Kikuchi et al., *Planta*, 190:525-535 (1993)).

Suitable oligomannosides for use in the methods of the present invention include, without limitation, an oligomannoside having the mannotetraose Man(1-3) Man(1-2) Man(1-2) Man. Such an oligomannoside can be purified from PPM as described in, e.g., Faille et al., supra. An exemplary neoglycolipid specific for ASCA can be constructed by releasing the oligomannoside from its respective PPM and subsequently coupling the released oligomannoside to 4-hexadecylaniline or the like.

The determination of anti-OmpC antibody levels in a sample is also useful in the present invention. As used herein, the term "anti-outer membrane protein C antibody" or "anti-OmpC antibody" includes antibodies directed to a bacterial outer membrane porin as described in, e.g., U.S. Pat. No. 7,138,237. The term "outer membrane protein C" or "OmpC" includes a bacterial porin that is immunoreactive with an anti-OmpC antibody.

The level of anti-OmpC antibody present in a sample from an individual can be determined using an OmpC protein or a fragment thereof such as an immunoreactive fragment thereof. Suitable OmpC antigens useful in determining anti-OmpC antibody levels in a sample include, without limitation, an OmpC protein, an OmpC polypeptide having substantially the same amino acid sequence as the OmpC protein, or a fragment thereof such as an immunoreactive fragment thereof. As used herein, an OmpC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpC protein, with the amino acid identity determined using a sequence alignment program such as CLUSTALW. Such antigens can be prepared, for example, by purification from enteric bacteria such as *E. coli*, by recombinant expression of a nucleic acid such as Genbank Accession No. K00541, by synthetic means such as solution or solid phase peptide synthesis, or by using phage display.

The determination of anti-I2 antibody levels in a sample is also useful in the present invention. As used herein, the term "anti-I2 antibody" includes antibodies directed to a microbial antigen sharing homology to bacterial transcriptional regulators as described in, e.g., U.S. Pat. No. 6,309,643. The term "I2" includes a microbial antigen that is immunoreactive with an anti-I2 antibody. The microbial I2 protein is a polypeptide of 100 amino acids sharing some similarity weak homology with the predicted protein 4 from *C. pasteurianum*, Rv3557c from *Mycobacterium tuberculosis*, and a transcriptional regulator from *Aquifex aeolicus*. The nucleic acid and protein sequences for the I2 protein are described in, e.g., U.S. Pat. No. 6,309,643.

The level of anti-I2 antibody present in a sample from an individual can be determined using an I2 protein or a fragment thereof such as an immunoreactive fragment thereof. Suitable I2 antigens useful in determining anti-I2 antibody levels in a sample include, without limitation, an I2 protein, an I2 polypeptide having substantially the same amino acid sequence as the I2 protein, or a fragment thereof such as an immunoreactive fragment thereof. Such I2 polypeptides exhibit greater sequence similarity to the I2 protein than to the *C. pasteurianum* protein 4 and include isotype variants and homologs thereof. As used herein, an I2 polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring I2 protein, with the amino acid identity determined using a sequence alignment program such as CLUSTALW. Such I2 antigens can be prepared, for example, by purification from microbes, by recombinant expression of a nucleic acid encoding an I2 antigen, by synthetic means such as solution or solid phase peptide synthesis, or by using phage display.

The determination of anti-flagellin antibody levels in a sample is also useful in the present invention. As used herein, the term "anti-flagellin antibody" includes antibodies directed to a protein component of bacterial flagella as described in, e.g., PCT Patent Publication No. WO 03/053220 and U.S. Patent Publication No. 20040043931. The term "flagellin" includes a bacterial flagellum protein that is immunoreactive with an anti-flagellin antibody. Microbial flagellins are proteins found in bacterial flagellum that arrange themselves in a hollow cylinder to form the filament.

The level of anti-flagellin antibody present in a sample from an individual can be determined using a flagellin protein or a fragment thereof such as an immunoreactive fragment thereof. Suitable flagellin antigens useful in determining anti-flagellin antibody levels in a sample include, without limitation, a flagellin protein such as Cbir-1 flagellin, flagellin X, flagellin A, flagellin B, fragments thereof, and combinations thereof, a flagellin polypeptide having substantially the same amino acid sequence as the flagellin protein, or a fragment thereof such as an immunoreactive fragment thereof. As used herein, a flagellin polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring flagellin protein, with the amino acid identity determined using a sequence alignment program such as CLUSTALW. Such flagellin antigens can be prepared, e.g., by purification from bacterium such as *Helicobacter Bilis, Helicobacter mustelae, Helicobacter pylori, Butyrivibrio fibrisolvens*, and bacterium found in the cecum, by recombinant expression of a nucleic acid encoding a flagellin antigen, by synthetic means such as solution or solid phase peptide synthesis, or by using phage display.

The determination of the presence or level of lactoferrin in a sample is also useful in the present invention. In certain instances, the presence or level of lactoferrin is detected at the level of mRNA expression with an assay such as, for example, a hybridization assay or an amplification-based assay. In certain other instances, the presence or level of lactoferrin is detected at the level of protein expression using, for example, an immunoassay (e.g., ELISA) or an immunohistochemical assay. An ELISA kit available from Calbiochem (San Diego, Calif.) can be used to detect human lactoferrin in a plasma, urine, bronchoalveolar lavage, or cerebrospinal fluid sample. Similarly, an ELISA kit available from U.S. Biological (Swampscott, Mass.) can be used to determine the level of lactoferrin in a plasma sample. Likewise, ELISA kits available from TECHLAB, Inc. (Blacksburg, Va.) can be used to determine the level of lactoferrin in a stool sample. Additionally, U.S. Patent Publication No. 20040137536 describes an ELISA assay for determining the presence of elevated lactoferrin levels in a stool sample, and U.S. Patent Publication No. 20040033537 describes an ELISA assay for determining the concentration of endogenous lactoferrin in a stool, mucus, or bile sample. In some embodiments, then presence or level of anti-lactoferrin antibodies can be detected in a sample using, e.g., lactoferrin protein or a fragment thereof.

The determination of the presence or level of C-reactive protein (CRP) in a sample is also useful in the present invention. In certain instances, the presence or level of CRP is detected at the level of mRNA expression with an assay such as, for example, a hybridization assay or an amplification-based assay. In certain other instances, the presence or level of CRP is detected at the level of protein expression using, for example, an immunoassay (e.g., ELISA) or an immunohistochemical assay. For example, a sandwich colorimetric ELISA assay available from Alpco Diagnostics (Salem, N.H.) can be used to determine the level of CRP in a serum, plasma, urine, or stool sample. Similarly, an ELISA kit available from Biomeda Corporation (Foster City, Calif.) can be used to detect CRP levels in a sample. Other methods for determining CRP levels in a sample are described in, e.g., U.S. Pat. Nos. 6,838,250 and 6,406,862; and U.S. Patent Publication Nos. 20060024682 and 20060019410.

In addition, hemoccult, fecal occult blood, is often indicative of gastrointestinal illness and various kits have been developed to monitor gastrointestinal bleeding. For example, Hemoccult SENSA, a Beckman Coulter product, is a diagnostic aid for gastrointestinal bleeding, iron deficiency, peptic ulcers, ulcerative colitis, and, in some instances, in screening for colorectal cancer. This particular assay is based on the oxidation of guaiac by hydrogen peroxide to produce a blue color. A similar colorimetric assay is commercially available from Helena Laboratories (Beaumont, Tex.) for the detection of blood in stool samples. Other methods for detecting occult blood in a stool sample by determining the presence or level of hemoglobin or heme activity are described in, e.g., U.S. Pat. Nos. 4,277,250, 4,920,045, 5,081,040, and 5,310,684.

Calprotectin is a calcium and zinc-binding protein found in all cells, tissues, and fluids in the body. Calprotectin is a major protein in neutrophilic granulocytes and macrophages and accounts for as much as 60% of the total protein in the cytosolic fraction of these cells. It is therefore a surrogate marker of neutrophil turnover. Its concentration in stool correlates with the intensity of neutrophil infiltration of the intestinal mucosa and with the severity of inflammation. Calprotectin can be measured with an ELISA using small (50-100 mg) fecal samples (see, e.g., Johne et al., *Scand J Gastroenterol.*, 36:291-296 (2001)).

The determination of the presence of polymorphisms in the NOD2/CARD15 gene in a sample is also useful in the present invention. For example, polymorphisms in the NOD2 gene such as a C2107T nucleotide variant that results in a R703W protein variant can be identified in a sample from an individual (see, e.g., U.S. Patent Publication No. 20030190639). In an alternative embodiment, NOD2 mRNA levels can be used as a diagnostic marker of the present invention to aid in classifying IBD.

VI. Assays

Any of a variety of assays, techniques, and kits known in the art can be used to determine the presence or level of IgA anti-OmpA antibodies, IgA anti-OmpC antibodies, or one or more markers in a sample to classify or identify whether the sample is associated with IBD or a clinical subtype thereof such as Crohn's Disease.

The present invention relies, in part, on determining the presence or level of IgA anti-OmpA antibodies, or at least one marker in a sample obtained from an individual. As used herein, the term "determining the presence of at least one marker" includes determining the presence of each marker of interest by using any quantitative or qualitative assay known to one of skill in the art. In certain instances, qualitative assays that determine the presence or absence of a particular trait, variable, or biochemical or serological substance (e.g., protein or antibody) are suitable for detecting each marker of interest. In certain other instances, quantitative assays that determine the presence or absence of RNA, protein, antibody, or activity are suitable for detecting each marker of interest. As used herein, the term "determining the level of at least one marker" includes determining the level of each marker of interest by using any direct or indirect quantitative assay known to one of skill in the art. In certain instances, quantitative assays that determine, for example, the relative or absolute amount of RNA, protein, antibody, or activity are suitable for determining the level of each marker of interest. One skilled in the art will appreciate that any assay useful for determining the level of a marker is also useful for determining the presence or absence of the marker.

As used herein, the term "antibody" includes a population of immunoglobulin molecules, which can be polyclonal or monoclonal and of any isotype, or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

Flow cytometry can be used to determine the presence or level of one or more markers in a sample. Such flow cytometric assays, including bead based immunoassays, can be used to determine, e.g., antibody marker levels in the same manner as described for detecting serum antibodies to *Candida albicans* and HIV proteins (see, e.g., Bishop et al., *J. Immunol. Methods*, 210:79-87 (1997); McHugh et al., *J. Immunol. Methods*, 116:213 (1989); Scillian et al., *Blood*, 73:2041 (1989)).

Phage display technology for expressing a recombinant antigen specific for a marker can also be used to determine the presence or level of one or more markers in a sample. Phage particles expressing an antigen specific for, e.g., an antibody marker can be anchored, if desired, to a multi-well plate using an antibody such as an anti-phage monoclonal antibody (Felici et al., "Phage-Displayed Peptides as Tools for Characterization of Human Sera" in Abelson (Ed.), *Methods in Enzymol.*, 267, San Diego: Academic Press, Inc. (1996)).

A variety of immunoassay techniques, including competitive and non-competitive immunoassays, can be used to determine the presence or level of one or more markers in a sample (see, e.g., Self et al., *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis*, 18:2184-2193 (1997); Bao, *J. Chromatogr. B. Biomed. Sci.*, 699:463-480 (1997)). Liposome immunoassays, such as flow-injection liposome immunoassays and liposome immunosensors, are also suitable for use in the present invention (see, e.g., Rongen et al., *J. Immunol. Methods*, 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, Calif.; Kit #449430) and can be performed using a Behring Nephelometer Analyzer (Fink et al., *J. Clin. Chem. Clin. Biol. Chem.*, 27:261-276 (1989)).

Antigen capture ELISA can be useful for determining the presence or level of one or more markers in a sample. For example, in an antigen capture ELISA, an antibody directed to a marker of interest is bound to a solid phase and sample is added such that the marker is bound by the antibody. After unbound proteins are removed by washing, the amount of bound marker can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the marker of interest is allowed to bind to the first antibody. The amount of the marker is quantitated by measuring the amount of a second antibody that binds the marker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for determining the presence or level of one or more markers in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

The immunoassays described above are particularly useful for determining the presence or level of one or more markers in a sample. As a non-limiting example, a fixed neutrophil ELISA is useful for determining whether a sample is positive for ANCA or for determining ANCA levels in a sample. Similarly, an ELISA using yeast cell wall phosphopeptidomannan is useful for determining whether a sample is positive for ASCA-IgA and/or ASCA-IgG, or for determining ASCA-IgA and/or ASCA-IgG levels in a sample. An ELISA using OmpC protein or a fragment thereof is useful for determining whether a sample is positive for anti-OmpC antibodies, or for determining anti-OmpC antibody levels in a sample. Similarly, an ELISA using OmpA protein or a fragment thereof is useful for determining whether a sample is positive for anti-OmpA antibodies, or for determining anti-OmpA antibody levels in a sample. An ELISA using I2 protein or a fragment thereof is useful for determining whether a sample is positive for anti-I2 antibodies, or for determining anti-I2 antibody levels in a sample. An ELISA using flagellin protein or a fragment thereof is useful for determining whether a sample is positive for anti-flagellin antibodies, or for determining anti-flagellin antibody levels in a sample. In addition, the immunoassays described above are particularly useful for determining the presence or level of other markers in a sample.

Specific immunological binding of the antibody to the marker of interest can be detected directly or indirectly. Direct labels include fluorescent or luminescent tags, metals, dyes, radionuclides, and the like, attached to the antibody. An antibody labeled with iodine-125 ($^{125}$I) can be used for determining the levels of one or more markers in a sample. A chemiluminescence assay using a chemiluminescent antibody specific for the marker is suitable for sensitive, non-radioactive detection of marker levels. An antibody labeled with fluorochrome is also suitable for determining the levels of one or more markers in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

Quantitative western blotting can also be used to detect or determine the presence or level of one or more markers in a sample. Western blots can be quantitated by well-known methods such as scanning densitometry or phosphorimaging. As a non-limiting example, protein samples are electrophoresed on 10% SDS-PAGE Laemmli gels. Primary murine monoclonal antibodies are reacted with the blot, and antibody binding can be confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.*, 28:669-675 (1998).

Alternatively, a variety of immunohistochemical assay techniques can be used to determine the presence or level of one or more markers in a sample. The term immunohistochemical assay encompasses techniques that utilize the visual detection of fluorescent dyes or enzymes coupled (i.e., conjugated) to antibodies that react with the marker of interest using fluorescent microscopy or light microscopy and includes, without limitation, direct fluorescent antibody assay, indirect fluorescent antibody (IFA) assay, anticomplement immunofluorescence, avidin-biotin immunofluorescence, and immunoperoxidase assays. An IFA assay, for example, is useful for determining whether a sample is positive for ANCA, the level of ANCA in a sample, whether a sample is positive for pANCA, the level of pANCA in a sample, and/or an ANCA staining pattern (e.g., cANCA, pANCA, NSNA, and/or SAPPA staining pattern). The concentration of ANCA in a sample can be quantitated, e.g., through endpoint titration or through measuring the visual intensity of fluorescence compared to a known reference standard.

Alternatively, the presence or level of a marker of interest can be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, tandem MS, etc.). Qualitative or quantitative detection of a marker of interest can also be determined by well-known methods including, without limitation, Bradford assays, Coomassie blue staining, silver staining, assays for radiolabeled protein, and mass spectrometry.

The analysis of a plurality of markers may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of markers on a single surface. Particularly useful physical formats comprise surfaces having a plurality of discrete, addressable locations for the detection of a plurality of different markers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

In addition to the above-described assays for determining the presence or level of various markers of interest, analysis of marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., *Current Protocols in Molecular Biology*, John Wiley & Sons, Inc. New York (1999), Chapter 7 and Supplement 47; Theophilus et al., "PCR Mutation Detection Protocols," Humana Press, (2002); and Innis et al., *PCR Protocols*, San Diego, Academic Press, Inc. (1990). General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of the genotype of a marker such as a genetic marker can be performed using techniques known in the art including, without limitation, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques,* 13:626-633 (1992)), solid-phase sequencing (Zimmerman et al., *Methods Mol. Cell. Biol.,* 3:39-42 (1992)), sequencing with mass spectrometry such as matrix-assisted laser desorption/ionization time-of-flight mass spectrometry (MALDI-TOF/MS; Fu et al., *Nature Biotech.,* 16:381-384 (1998)), and sequencing by hybridization (Chee et al., *Science,* 274:610-614 (1996); Drmanac et al., *Science,* 260:1649-1652 (1993); Drmanac et al., *Nature Biotech.,* 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for genotyping an individual at a polymorphic site in a marker include, e.g., the INVADER® assay from Third Wave Technologies, Inc., restriction fragment length polymorphism (RFLP) analysis, allele-specific oligonucleotide hybridization, a heteroduplex mobility assay, and single strand conformational polymorphism (SSCP) analysis.

Several markers of interest may be combined into one test for efficient processing of a multiple of samples. In addition, one skilled in the art would recognize the value of testing multiple samples (e.g., at successive time points, etc.) from the same subject. Such testing of serial samples can allow the identification of changes in marker levels over time. Increases or decreases in marker levels, as well as the absence of change in marker levels, can also provide useful information to classify IBD or to differentiate between clinical subtypes of IBD.

A panel consisting of one or more of the markers described above may be constructed to provide relevant information related to the approach of the present invention for classifying a sample as being associated with IBD or a clinical subtype thereof. Such a panel may be constructed using 1, 2, 3, 4, 5, 6, 7, 8, 9, 10, 11, 12, 13, 14, 15, 16, 17, 18, 19, 20, 25, 30, 35, 40, or more individual markers. The analysis of a single marker or subsets of markers can also be carried out by one skilled in the art in various clinical settings. These include, but are not limited to, ambulatory, urgent care, critical care, intensive care, monitoring unit, inpatient, outpatient, physician office, medical clinic, and health screening settings.

The analysis of markers could be carried out in a variety of physical formats as well. For example, the use of microtiter plates or automation could be used to facilitate the processing of large numbers of test samples. Alternatively, single sample formats could be developed to facilitate treatment and diagnosis in a timely fashion.

VII. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Preparation and Characterization of Omp Antigens

This example illustrates the preparation and characterization of Omp antigens such as OmpA and OmpC using spheroplast lysis.

Production of Omp Antigens by Bacterial Cell Fermentation: Omp antigens were produced by fermentation of *E. coli* strain MC4100 in a 5 L vessel. The fermented bacterial cells were harvested by centrifugation and washed twice with ice-cold 20 mM Tris-HCl, pH 7.4.

Digestion of Bacterial Cell Wall and Formation and Lysis of Spheroplasts: The harvested cell paste was suspended in cold spheroplast-forming buffer (20% sucrose, 20 mM Tris-HCl, pH 7.4, 1 mg/mL lysozyme) with occasional mixing for 1 hr. The formed spheroplasts were then lysed by 14-fold dilution into ice-cold 10 mM Tris-HCl, pH 7.4+0.1 mg/mL of DNase-I with stirring for 10 min. The lysed bacterial cells were again harvested by centrifugation.

Fragmentation of the Bacterial Cell Membrane and Harvesting of the Membrane Fraction: The lysed bacterial cell pellet was suspended in ice-cold 10 mM Tris-HCl, pH 7.4+0.1 mg/mL DNase-I and stirred for 10 min, followed by pulse sonication twice to fragment the cell membrane. The resulting cell debris was removed by centrifugation and the membrane fraction harvested by ultracentrifugation.

Removal of Weakly Bound Cell Membrane Proteins from the Membrane Fraction: The harvested membrane fraction was resuspended in 20 mM Tris-HCl, pH 7.4+1% Sodium Dodecyl Sulfate (SDS) and then stirred at 37° C. for 90 min. The 1% SDS-extracted membrane fraction was again recovered by ultracentrifugation and the supernatant saved.

Extraction of Omp Antigens from the Pre-Extracted Membrane Fraction: The recovered pre-extracted membrane fraction was resuspended in 20 mM Tris-HCl, pH 7.4+3% SDS+0.5M NaCl and then stirred at 37° C. for 1 hr. The membrane debris was again removed by ultracentrifugation and the extracted Omp antigens in the supernatant were purified by dialysis against 0.2% Triton X-100 in 20 mM Tris-HCl, pH 7.4, followed by dialysis against 0.1% Triton X-100 in 20 mM Tris-HCl, pH 7.4 and, finally, dialysis against 0.05% Triton X-100 in 20 mM Tris-HCl, pH 7.4.

Characterization of the Isolated Omp Antigens: The purity of the dialyzed Omp antigens (e.g., OmpA and OmpC) was determined by SDS-PAGE analysis and the identity of the Omp antigens was verified by amino acid sequence analysis. The immuno-reactivity of the Omp antigens was determined by Western blotting.

The Omp purification protocol described herein provides a preparation enriched in OmpA and OmpC antigens, as indicated by the presence of a 37 kDa doublet upon SDS-PAGE analysis of the dialyzed Omp antigen preparation. The identity of the lower band of the 37 kDa doublet as OmpA (SEQ ID NO:1) and the upper band of the 37 kDa doublet as OmpC (SEQ ID NO:2) was confirmed by amino acid sequence analysis. Briefly, Omp proteins were separated by SDS-PAGE, transferred to PVDF membrane, and subjected to amino acid sequence analysis.

Example 2

Preparation of Recombinant OmpA Antigen

This example provides an exemplary protocol for the cloning and expression of His-OmpA in *E. coli*.

Gene synthesis and construct subcloning: OmpA DNA was synthesized based on the original *E. coli* K-12 OmpA nucleic acid sequence (GenBank Accession No. V00307.1). A 6×His (SEQ ID NO:4) tag replaced the signal peptide of the original sequence. The synthesized OmpA DNA was subcloned into pET24a (Novagen) between the NcoI and XhoI sites. The final construct, pET-His-OmpA, has the following nucleotide coding sequence and amino acid sequence, with the underlined amino acid sequence representing the His-tag.

pET-His-OmpA nucleotide sequence (SEQ ID NO:5):

```
atggcgcaccatcaccaccatcacgccgctccgaaagataacacctggtac
actggtgctaaactgggctggtcccagtaccatgatactggtttcatcaac
aacaatggcccgacccatgaaaaccaactgggcgctggtgcttttggtggt
taccaggttaacccgtatgttggctttgaaatgggttacgactggttaggt
cgtatgccgtacaaaggcagcgttgaaaacggtgcatacaaagctcagggc
gttcaactgaccgctaaactgggttacccaatcactgacgacctggacatc
tacactcgtctgggtggcatggtatggcgtgcagacactaaatccaacgtt
tatggtaaaaaccacgacaccggcgtttctccggtcttcgctggcggtgtt
gagtacgcgatcactcctgaaatcgctacccgtctggaataccagtggacg
aacaacatcggtgacgcacacaccatcggcactcgtccggacaacggcatg
ctgagcctgggtgtttcctaccgtttcggtcagggcgaggcagctccagta
gttgctccggctccagctccggcaccggaagtacagaccaagcacttcact
ctgaagtctgacgttctgttcaacttcaacaaagcaaccctgaaaccggaa
ggtcaggctgctctggatcagctgtacagccagctgagcaacttggatccg
aaagacggttccgtagttgttctgggttacaccgaccgcatcggttctgac
gcttacaaccagggtctgtccgagcgccgtgctcagtctgttgttgattac
ctgatctccaaaggtatcccggcagacaagatctccgcacgtggtatgggc
gaatcaacccggttactggcaacacctgtgacaacgtgaaacagcgtgct
gcactgatcgactgcctggctccggatcgtcgcgtagagatcgaagttaaa
ggtatcaaagacgttgtaactcagccgcaggcttaa
``` pET-His-OmpA amino acid sequence (SEQ ID NO:6):

MAHHHHHHAAPKDNTWYTGAKLGWSQYHDTGFINNNGPTHENQLGAGAFGG

YQVNPYVGFEMGYDWLGRMPYKGSVENGAYKAQGVQLTAKLGYPITDDLDI

YTRLGGMVWRADTKSNVYGKNHDTGVSPVFAGGVEYAITPEIATRLEYQWT

NNIGDAHTIGTRPDNGMLSLGVSYRFGQGEAAPVVAPAPAPAPEVQTKHFT

LKSDVLFNFNKATLKPEGQAALDQLYSQLSNLDPKDGSVVVLGYTDRIGSD

AYNQGLSERRAQSVVDYLISKGIPADKISARGMGESNPVTGNTCDNVKQRA

ALIDCLAPDRRVEIEVKGIKDVVTQPQA

E. coli expression: Constructs of His-OmpA were transformed into BL21(DE3) and BL21(DE3)-GroE strains (Accelagen). The transformed strains were tested for total and soluble expression of His-OmpA under several conditions. Most of the proteins were insoluble under all conditions tested. Both strains gave similar expression levels of His-OmpA. Inclusion bodies from transformed BL21(DE3)-GroE were made, proteins were solubilized in 6M urea, and then purified by Ni affinity chromatography. N-terminal sequencing confirmed the identity of the recombinant His-OmpA antigen: AHHHHHHAAPKDNTW (SEQ ID NO:7).

FIG. 1 illustrates an analysis of recombinant His-OmpA by SDS-PAGE and Western blotting. In particular, FIG. 1 shows that His-OmpA antigen was highly sensitive and immuno-reactive against IgA anti-OmpA antibodies in pooled Crohn's disease patient sera that were also positive for IgA anti-OmpC antibodies.

Example 3

Determination of Anti-Omp Antibody Levels

This example illustrates an exemplary immunoassay (e.g., ELISA) for measuring anti-Omp (e.g., IgA anti-OmpA and/or IgA anti-OmpC) antibody levels in a sample such as a serum sample.

The Omp immunoassay (e.g., ELISA) can be performed essentially as follows. Plates are coated overnight at 4° C. with Omp antigen (e.g., 1000/well at 0.25 μg/ml) in borate buffered saline, pH 8.5. Exemplary Omp antigens include, but are not limited to, the OmpA and OmpC-enriched antigen preparation described in Example 1, one or more fractions of OmpA and/or OmpC antigens purified (e.g., by chromatography and/or gel filtration) from the Omp antigen preparation described in Example 1, or recombinant OmpA and/or OmpC antigens such as His-OmpA and/or His-OmpC. After three washes in 0.05% Tween 20 in phosphate buffered saline (PBS), the plates are blocked with 150 μl/well of 0.5% bovine serum albumin in PBS, pH 7.4 (BSA-PBS) for 30 minutes at room temperature. The blocking solution is then replaced with 100 μl/well of Crohn's disease, ulcerative colitis, or normal control serum, diluted 1:100. The plates are then incubated for 2 hours at room temperature and washed as before. Alkaline phosphatase-conjugated goat anti-human IgA (α-chain specific) or IgG (γ-chain specific) (Jackson ImmunoResearch; West Grove, Pa.) is added to the plates at a dilution of 1:1000 in BSA-PBS. The plates are incubated for 2 hours at room temperature before washing three times with 0.05% Tween 20/PBS followed by another three washes with Tris-buffered normal saline, pH 7.5. Substrate solution (e.g., 1.5 mg/ml disodium p-nitrophenol phosphate in 2.5 mM $MgCl_2$, 0.01M Tris, pH 8.6) is added at 1000/well, and color is allowed to develop for one hour. The plates are then analyzed at 405 nm. In certain instances, anti-Omp-positive reactivity (e.g., IgA anti-OmpA-positive reactivity and/or IgA anti-OmpC-positive reactivity) is defined as reactivity greater than two standard deviations above the mean reactivity obtained with control (normal) or ulcerative colitis sera analyzed at the same time as the test samples.

Figure 2:
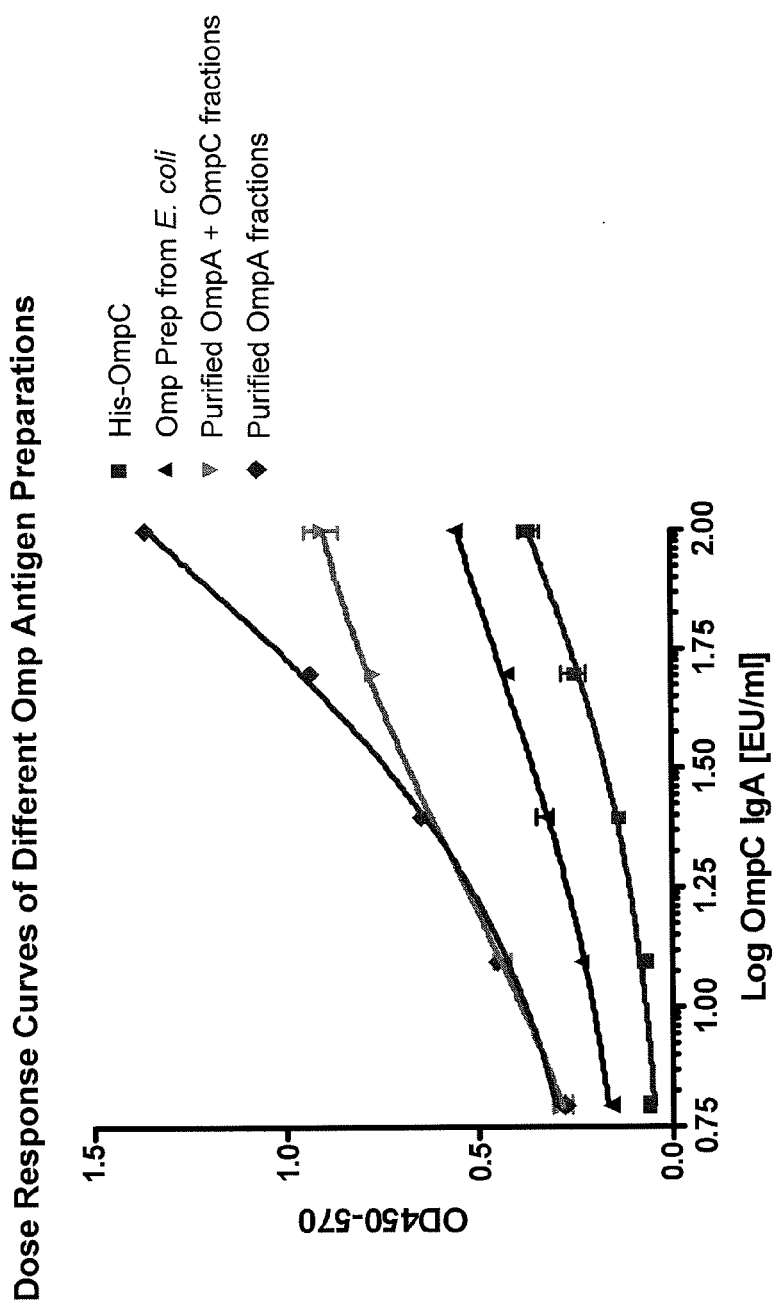
FIG. 2 illustrates a dose response curve of different Omp antigen preparations. OmpA antigen purified from the Omp antigen preparation described in Example 1 ("Purified OmpA fractions") displayed a high level of sensitivity and immuno-reactivity against IgA anti-OmpA antibodies in pooled Crohn's disease patient sera that were also positive for IgA anti-OmpC antibodies.

FIG. 2 shows dose response curves of IgA anti-Omp antibodies (e.g., IgA anti-OmpA and/or IgA anti-OmpC antibodies) in different Omp antigen preparations as measured by ELISA. The human serum samples used in the assays were pooled Crohn's disease patient sera that were positive for IgA anti-OmpC antibodies. Different dilutions of pooled IgA OmpC-positive human serum were used in the ELISA. An IgA OmpC standard was used to make the dilutions α-axis). The arbitrary ELISA unit (EU/ml) was defined as 100 EU/ml, which is equivalent to a 1:100 dilution of the pooled IgA OmpC-positive human serum (i.e., IgA OmpC standard), and can be used to define the IgA OmpA standard. In particular, FIG. 2 demonstrates that OmpA antigen purified from the Omp antigen preparation described in Example 1 ("Purified OmpA fractions") displayed a high level of sensitivity and immuno-reactivity against IgA anti-OmpA antibodies in pooled Crohn's disease patient sera that were positive for IgA anti-OmpC antibodies. Both the OmpA and OmpC-enriched antigen preparation described in Example 1 ("Omp Prep from E. coli") and recombinant OmpC antigen ("His-OmpC") generated a positive signal with pooled Crohn's disease patient sera positive for IgA anti-OmpC antibodies. The use of a combination of OmpA and OmpC antigens purified from the Omp antigen preparation described in Example 1 ("Purified OmpA+OmpC fractions") provided a level of sensitivity and immuno-reactivity that was greater than the level obtained with the crude Omp prep from E. coli or with His-OmpC.

Figure 3:
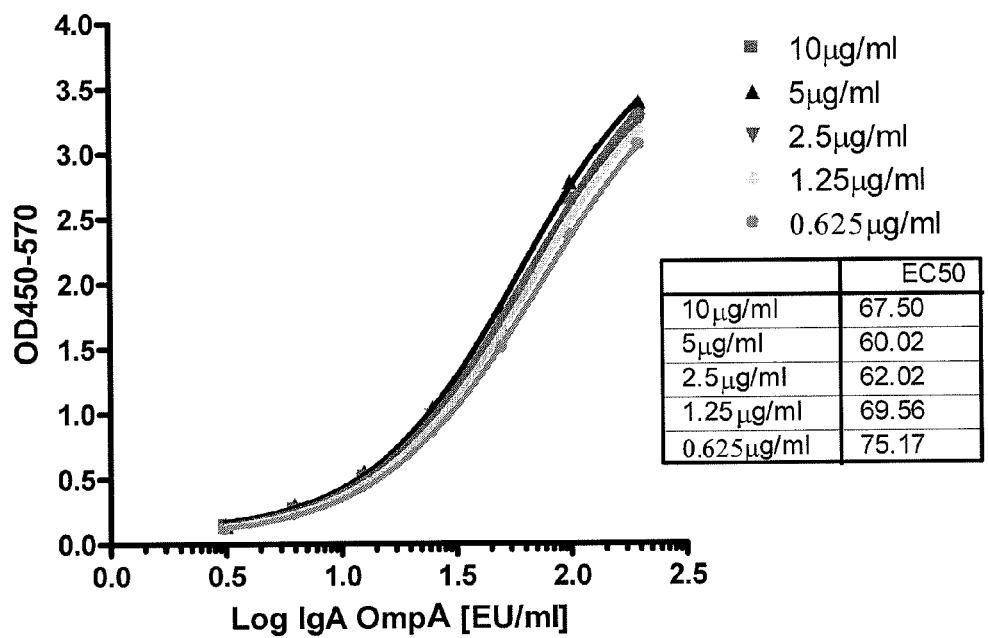
FIG. 3 illustrates a dose response curve of IgA anti-OmpA with different amounts of His-OmpA antigen by ELISA. All concentrations of His-OmpA antigen tested (ranging from 0.625 µg/ml to 10 µg/ml) provided high sensitivity and immuno-reactivity against IgA anti-OmpA antibodies in pooled Crohn's disease patient sera that were also positive for IgA anti-OmpC antibodies as indicated by the EC50 values observed for each His-OmpA antigen concentration.
Figure 4:
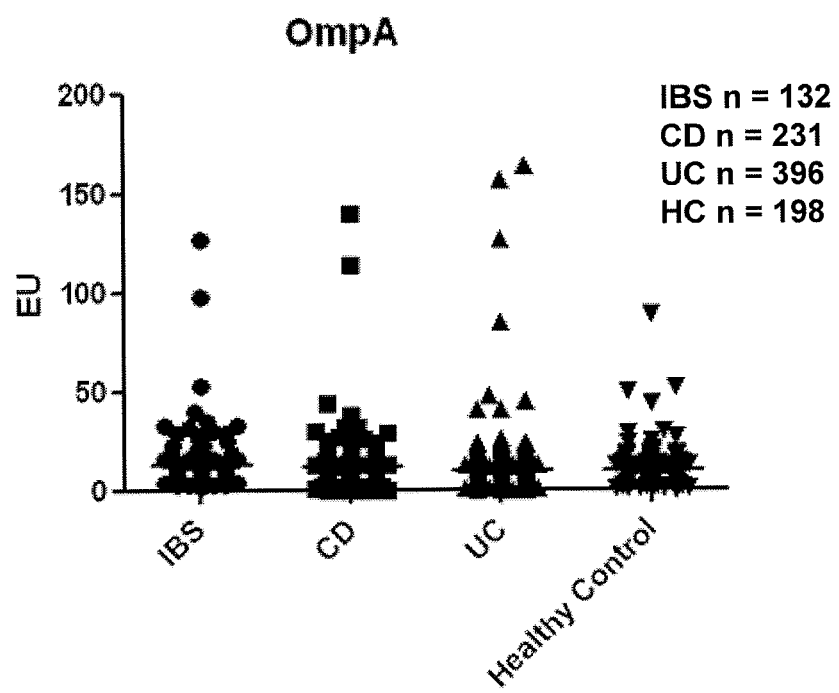
FIG. 4 illustrates a determination of anti-OmpA antibody levels in clinical samples from Crohn's disease (CD) and ulcerative colitis (UC) patient groups as well as the non-IBD irritable bowel syndrome (IBS) and healthy control (HC) patient groups.

FIG. 3 illustrates a dose response curve of IgA anti-OmpA with different amounts of His-OmpA antigen by ELISA. Specifically, different amounts of purified His-OmpA were coated onto an immuno-plate (e.g., 10 µg/ml, 1:2 dilutions, 100 µl/well). The plate was blocked and incubated with different dilutions of Crohn's disease patient sera positive for IgA anti-OmpC antibodies (e.g., 200 EU/ml, 1:2 dilutions). HRP-labeled goat anti-human IgA was used to detect the antibody bound to His-OmpA. FIG. 3 shows that all His-OmpA antigen amounts tested (ranging from 0.625 µg/ml to 10 µg/ml) provided high sensitivity and immuno-reactivity against IgA anti-OmpA antibodies in patient sera that were also positive for IgA anti-OmpC antibodies as indicated by the low half maximal effective concentration (EC50) values observed for each His-OmpA antigen concentration.

Example 4

Determination of ASCA Levels

This example illustrates the preparation of yeast cell well mannan and an analysis of ASCA levels in a sample such as a serum sample using an immunoassay such as an ELISA.

Yeast cell wall mannan can be prepared as described in Faille et al., *Eur. J. Clin. Microbiol. Infect. Dis.*, 11:438-446 (1992) and in Kocourek et al., *J. Bacteriol.*, 100:1175-1181 (1969). Briefly, a lyophilized pellet of yeast *Saccharomyces uvarum* is obtained from the American Type Culture Collection (#38926). Yeast are reconstituted in 10 ml 2×YT medium, prepared according to Sambrook et al., In "Molecular Cloning," Cold Spring Harbor Laboratory Press (1989). *S. uvarum* are grown for two to three days at 30° C. The terminal *S. uvarum* culture is inoculated on a 2×YT agar plate and subsequently grown for two to three days at 30° C. A single colony is used to inoculate 500 ml 2×YT media, and grown for two to three days at 30° C. Fermentation media (pH 4.5) is prepared by adding 20 g glucose, 2 g bacto-yeast extract, 0.25 g $MgSO_4$, and 2.0 ml 28% $H_3PO_4$ per liter of distilled water. The 500 ml culture is used to inoculate 50 liters of fermentation media, and the culture fermented for three to four days at 37° C.

*S. uvarum* mannan extract is prepared by adding 50 ml 0.02 M citrate buffer (5.88 g/l sodium citrate; pH 7.0±0.1) to each 100 g of cell paste. The cell/citrate mixture is autoclaved at 125° C. for ninety minutes and allowed to cool. After centrifuging at 5000 rpm for 10 minutes, the supernatant is removed and retained. The cells are then washed with 75 ml 0.02 M citrate buffer and the cell/citrate mixture again autoclaved at 125° C. for ninety minutes. The cell/citrate mixture is centrifuged at 5000 rpm for 10 minutes, and the supernatant is retained.

In order to precipitate copper/mannan complexes, an equal volume of Fehling's Solution is added to the combined supernatants while stirring. The complete Fehling's solution is prepared by mixing Fehling's Solution A with Fehling's Solution B in a 1:1 ratio just prior to use. The copper complexes are allowed to settle, and the liquid decanted gently from the precipitate. The copper/mannan precipitate complexes are then dissolved in 6-8 ml 3N HCl per 100 grams yeast paste.

The resulting solution is poured with vigorous stirring into 100 ml of 8:1 methanol:acetic acid, and the precipitate allowed to settle for several hours. The supernatant is decanted and discarded, then the wash procedure is repeated until the supernatant is colorless, approximately two to three times. The precipitate is collected on a scintered glass funnel, washed with methanol, and air dried overnight. On some occasions, the precipitate is collected by centrifugation at 5000 rpm for 10 minutes before washing with methanol and air drying overnight. The dried mannan powder is dissolved in distilled water to a concentration of approximately 2 g/ml.

A *S. uvarum* mannan ELISA can be used to detect the presence or level of ASCA. For example, *S. uvarum* mannan ELISA plates can be saturated with antigen as follows. Purified *S. uvarum* mannan prepared as described above is diluted to a concentration of 100 µg/ml with phosphate buffered saline/0.2% sodium azide. Using a multi-channel pipettor, 100 µl of 100 µg/ml *S. uvarum* mannan is added per well to a Costar 96-well hi-binding plate (catalog no. 3590; Costar Corp., Cambridge, Mass.). The antigen is allowed to coat the plate at 4° C. for a minimum of 12 hours. Each lot of plates is compared to a previous lot before use. Plates are stored at 2-8° C. for up to one month.

Patient sera can be analyzed in duplicate for ASCA-IgA or ASCA-IgG reactivity. Microtiter plates saturated with antigen as described above are incubated with phosphate buffered saline/0.05% Tween-20 for 45 minutes at room temperature to inhibit nonspecific antibody binding. Patient sera are subsequently added at a dilution of 1:80 for analysis of ASCA-IgA and 1:800 for analysis of ASCA-IgG and incubated for 1 hour at room temperature. Wells are washed three times with PBS/0.05% Tween-20. Then, a 1:1000 dilution of alkaline phosphatase-conjugated goat anti-human IgA (Jackson Immunoresearch; West Grove, Pa.) or a 1:1000 dilution of alkaline phosphatase-conjugated goat anti-human IgG $F(ab')_2$ (Pierce; Rockford, Ill.) is added, and the microtiter plates are incubated for 1 hour at room temperature. A solution of p-nitrophenol phosphate in diethanolamine substrate buffer is added, and color development is allowed to proceed for 10 minutes. Absorbance at 405 nm is analyzed using an automated EMAX plate reader (Molecular Devices; Sunnyvale, Calif.).

To determine the base cut-off value for ASCA-IgA and ASCA-IgG, single point calibrators having fixed EU values can be used. For example, OD values for patient samples are compared to the OD value for the calibrators and multiplied by the calibrator assigned values. In some instances, the base cut-off value for ASCA-IgA ELISA is 20 EU. In other instances, the base cut-off value for ASCA-IgG is 40 EU.

Example 5

Determination of Anti-OmpA Antibody Levels in Clinical Samples

This example illustrates a determination of anti-OmpA antibody levels in clinical samples such as serum samples from Crohn's disease (CD), ulcerative colitis (UC), irritable bowel syndrome (IBS), and healthy control (HC) patient groups. In particular embodiments, the presence and/or level of anti-OmpA antibody is determined with an immunoassay (e.g., ELISA) such as the Omp immunoassay described in Example 3.

In certain instances, elevated anti-OmpA antibody levels include a level above a reference value of about 5.0, 10.0, 15.0, 20.0, 25.0, 30.0, 35.0, 40.0, 45.0, 50.0, 55.0, 60.0, 65.0, 70.0, 75.0, 80.0, 85.0, 90.0, or 100.0 EU or EU/ml (or any range or fraction therein) when an ELISA is used.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A diagnostic assay, said diagnostic assay comprising:

(a) determining the presence or absence of IgA anti-outer membrane protein A (anti-OmpA) antibodies in a sample by contacting said sample with an OmpA antigen or reactive fragment thereof, wherein said OmpA antigen or reactive fragment thereof is substantially-free of an OmpC antigen, under conditions suitable to form a complex of said OmpA antigen or reactive fragment thereof and IgA anti-OmpA antibody;

(b) contacting said complex with a labeled indicator antibody to form a labeled complex; and (c) detecting the presence or absence of said labeled complex with a detection device, wherein the presence of said labeled complex is associated with Crohn's disease.

2. The assay of claim 1, wherein said IgA anti-OmpA antibodies are detected with an enzyme-linked immunosorbent assay.

3. The assay of claim 1, further comprising determining the presence or absence of IgA anti-*Saccharomyces cerevisiae* antibodies (ASCA) in said sample, wherein the presence of IgA anti-OmpA antibodies or the presence of IgA ASCA in said sample is each independently associated with Crohn's disease.

4. The assay of claim 1, further comprising determining the presence or absence of IgA ASCA in said sample,
wherein the presence of both IgA anti-OmpA antibodies and IgA ASCA in said sample is associated with Crohn's disease.

5. The assay of claim 3, wherein the presence of IgA ASCA is determined by reactivity with purified yeast cell wall phosphopeptidomanan (PPM).

6. The assay of claim 5, wherein said yeast cell wall PPM is prepared from ATCC strain #38926.

7. The assay of claim 1, wherein said OmpA antigen is recombinant OmpA antigen.

8. The assay of claim 1, wherein said sample is human serum.

9. An assay kit for improving the diagnosis of Crohn's disease, said assay kit comprising:
(a) a plate well containing an OmpA antigen or reactive fragment thereof, wherein said OmpA antigen or reactive fragment thereof is substantially-free of an OmpC antigen;
(b) a labeled anti-IgA antibody; and
(c) instructions for detecting the presence or absence of IgA anti-OmpA antibodies in a patient's sample.

10. The assay kit of claim 9, wherein said sample is human serum.

11. An assay to aid in the detection of Crohn's disease comprising:
(a) contacting a sample with an OmpA antigen or reactive fragment thereof, wherein said OmpA antigen or reactive fragment thereof is substantially-free of OmpC antigen, under conditions suitable to transform said OmpA antigen or reactive fragment thereof into a complex comprising said OmpA antigen or reactive fragment thereof and IgA anti-OmpA antibody;
(b) contacting said complex with a labeled indicator antibody to transform said complex into a labeled complex; and
(c) detecting the presence of said IgA anti-OmpA antibodies in said sample.

12. The assay of claim 11, wherein said sample is human serum.

13. The assay of claim 11, wherein said assay is an ELISA assay.

14. The assay of claim 11, wherein detecting the presence of said IgA anti-OmpA antibodies in said sample comprises the use of a detection device.

15. The assay of claim 14, wherein said detection device comprises a spectrophotometer.

16. A method for performing an assay for improving the diagnosis of Crohn's disease, said method comprising:
(a) detecting the presence of IgA anti-OmpA antibodies in a patient's sample, wherein the IgA anti-OmpA antibodies are substantially-free of IgA anti-OmpC antibodies; and
(b) reporting the presence or absence of said IgA anti-OmpA antibodies in the patient's sample to improve the diagnosis of Crohn's disease.

17. The method of claim 16, wherein the detecting step is performed using an ELISA.

18. The method of claim 17, wherein the ELISA further comprises the steps of:
(a) contacting the sample with an OmpA antigen or reactive fragment thereof, wherein said OmpA antigen or reactive fragment thereof is substantially-free of an OmpC antigen;
(b) contacting the sample with a labeled anti-IgA antibody; and
(c) analyzing the sample using a spectrophotometer.

* * * * *

SEQUENCE LISTING

<160> NUMBER OF SEQ ID NOS: 7

<210> SEQ ID NO 1
<211> LENGTH: 346
<212> TYPE: PRT
<213> ORGANISM: Escherichia coli
<220> FEATURE:
<223> OTHER INFORMATION: Escherichia coli strain K-12 outer membrane
      protein A (OmpA, ompA), outer membrane protein II

<400> SEQUENCE: 1

```
Met Lys Lys Thr Ala Ile Ala Ile Ala Val Ala Leu Ala Gly Phe Ala
  1               5                  10                  15

Thr Val Ala Gln Ala Ala Pro Lys Asp Asn Thr Trp Tyr Thr Gly Ala
                 20                  25                  30

Lys Leu Gly Trp Ser Gln Tyr His Asp Thr Gly Phe Ile Asn Asn Asn
             35                  40                  45

Gly Pro Thr His Glu Asn Gln Leu Gly Ala Gly Ala Phe Gly Gly Tyr
 50                  55                  60

Gln Val Asn Pro Tyr Val Gly Phe Glu Met Gly Tyr Asp Trp Leu Gly
 65                  70                  75                  80

Arg Met Pro Tyr Lys Gly Ser Val Glu Asn Gly Ala Tyr Lys Ala Gln
                 85                  90                  95

Gly Val Gln Leu Thr Ala Lys Leu Gly Tyr Pro Ile Thr Asp Asp Leu
            100                 105                 110

Asp Ile Tyr Thr Arg Leu Gly Gly Met Val Trp Arg Ala Asp Thr Lys
            115                 120                 125

Ser Asn Val Tyr Gly Lys Asn His Asp Thr Gly Val Ser Pro Val Phe
130                 135                 140

Ala Gly Gly Val Glu Tyr Ala Ile Thr Pro Glu Ile Ala Thr Arg Leu
145                 150                 155                 160

Glu Tyr Gln Trp Thr Asn Asn Ile Gly Asp Ala His Thr Ile Gly Thr
                165                 170                 175

Arg Pro Asp Asn Gly Met Leu Ser Leu Gly Val Ser Tyr Arg Phe Gly
            180                 185                 190

Gln Gly Glu Ala Ala Pro Val Val Ala Pro Ala Pro Ala Pro Ala Pro
            195                 200                 205

Glu Val Gln Thr Lys His Phe Thr Leu Lys Ser Asp Val Leu Phe Asn
210                 215                 220

Phe Asn Lys Ala Thr Leu Lys Pro Glu Gly Gln Ala Ala Leu Asp Gln
225                 230                 235                 240

Leu Tyr Ser Gln Leu Ser Asn Leu Asp Pro Lys Asp Gly Ser Val Val
                245                 250                 255

Val Leu Gly Tyr Thr Asp Arg Ile Gly Ser Asp Ala Tyr Asn Gln Gly
            260                 265                 270

Leu Ser Glu Arg Arg Ala Gln Ser Val Val Asp Tyr Leu Ile Ser Lys
            275                 280                 285

Gly Ile Pro Ala Asp Lys Ile Ser Ala Arg Gly Met Gly Glu Ser Asn
290                 295                 300

Pro Val Thr Gly Asn Thr Cys Asp Asn Val Lys Gln Arg Ala Ala Leu
305                 310                 315                 320

Ile Asp Cys Leu Ala Pro Asp Arg Arg Val Glu Ile Glu Val Lys Gly
                325                 330                 335

Ile Lys Asp Val Val Thr Gln Pro Gln Ala
            340                 345
```

-continued

<210> SEQ ID NO 2
<211> LENGTH: 367
<212> TYPE: PRT
<213> ORGANISM: Escherichia coli
<220> FEATURE:
<223> OTHER INFORMATION: Escherichia coli strain K-12, substrain MG1655
     outer membrane porin protein C (OmpC, ompC), outer membrane
     protein 1b, b2215, ECK2207, JW2203, meoA, par

<400> SEQUENCE: 2

```
Met Lys Val Lys Val Leu Ser Leu Leu Val Pro Ala Leu Leu Val Ala
 1               5                  10                  15

Gly Ala Ala Asn Ala Ala Glu Val Tyr Asn Lys Asp Gly Asn Lys Leu
            20                  25                  30

Asp Leu Tyr Gly Lys Val Asp Gly Leu His Tyr Phe Ser Asp Asn Lys
        35                  40                  45

Asp Val Asp Gly Asp Gln Thr Tyr Met Arg Leu Gly Phe Lys Gly Glu
    50                  55                  60

Thr Gln Val Thr Asp Gln Leu Thr Gly Tyr Gly Gln Trp Glu Tyr Gln
65                  70                  75                  80

Ile Gln Gly Asn Ser Ala Glu Asn Glu Asn Asn Ser Trp Thr Arg Val
                85                  90                  95

Ala Phe Ala Gly Leu Lys Phe Gln Asp Val Gly Ser Phe Asp Tyr Gly
            100                 105                 110

Arg Asn Tyr Gly Val Val Tyr Asp Val Thr Ser Trp Thr Asp Val Leu
        115                 120                 125

Pro Glu Phe Gly Gly Asp Thr Tyr Gly Ser Asp Asn Phe Met Gln Gln
    130                 135                 140

Arg Gly Asn Gly Phe Ala Thr Tyr Arg Asn Thr Asp Phe Phe Gly Leu
145                 150                 155                 160

Val Asp Gly Leu Asn Phe Ala Val Gln Tyr Gln Gly Lys Asn Gly Asn
                165                 170                 175

Pro Ser Gly Glu Gly Phe Thr Ser Gly Val Thr Asn Asn Gly Arg Asp
            180                 185                 190

Ala Leu Arg Gln Asn Gly Asp Gly Val Gly Gly Ser Ile Thr Tyr Asp
        195                 200                 205

Tyr Glu Gly Phe Gly Ile Gly Gly Ala Ile Ser Ser Ser Lys Arg Thr
    210                 215                 220

Asp Ala Gln Asn Thr Ala Ala Tyr Ile Gly Asn Gly Asp Arg Ala Glu
225                 230                 235                 240

Thr Tyr Thr Gly Gly Leu Lys Tyr Asp Ala Asn Asn Ile Tyr Leu Ala
                245                 250                 255

Ala Gln Tyr Thr Gln Thr Tyr Asn Ala Thr Arg Val Gly Ser Leu Gly
            260                 265                 270

Trp Ala Asn Lys Ala Gln Asn Phe Glu Ala Val Ala Gln Tyr Gln Phe
        275                 280                 285

Asp Phe Gly Leu Arg Pro Ser Leu Ala Tyr Leu Gln Ser Lys Gly Lys
    290                 295                 300

Asn Leu Gly Arg Gly Tyr Asp Asp Glu Asp Ile Leu Lys Tyr Val Asp
305                 310                 315                 320

Val Gly Ala Thr Tyr Tyr Phe Asn Lys Asn Met Ser Thr Tyr Val Asp
                325                 330                 335

Tyr Lys Ile Asn Leu Leu Asp Asp Asn Gln Phe Thr Arg Asp Ala Gly
            340                 345                 350

Ile Asn Thr Asp Asn Ile Val Ala Leu Gly Leu Val Tyr Gln Phe
```

```
                                355                 360                 365

<210> SEQ ID NO 3
<211> LENGTH: 367
<212> TYPE: PRT
<213> ORGANISM: Escherichia coli
<220> FEATURE:
<223> OTHER INFORMATION: Escherichia coli outer membrane porin protein C
      (OmpC, ompC)

<400> SEQUENCE: 3

Met Lys Ser Lys Val Leu Ala Leu Leu Ile Pro Ala Leu Leu Ala Ala
1               5                   10                  15

Gly Ala Ala His Ala Ala Glu Val Tyr Asn Lys Asp Gly Asn Lys Leu
            20                  25                  30

Asp Leu Tyr Gly Lys Val Asp Gly Leu His Tyr Phe Ser Asp Asn Lys
        35                  40                  45

Asp Val Asp Gly Asp Gln Thr Tyr Met Arg Leu Gly Phe Lys Gly Glu
    50                  55                  60

Thr Gln Val Thr Asp Gln Leu Thr Gly Tyr Gly Gln Trp Glu Tyr Gln
65                  70                  75                  80

Ile Gln Gly Asn Ser Ala Glu Asn Glu Asn Asn Ser Trp Thr Arg Val
                85                  90                  95

Ala Phe Ala Gly Leu Lys Phe Gln Asp Val Gly Ser Phe Asp Tyr Gly
            100                 105                 110

Arg Asn Tyr Gly Val Val Tyr Asp Val Thr Ser Trp Thr Asp Val Leu
        115                 120                 125

Pro Glu Phe Gly Gly Asp Thr Tyr Gly Ser Asp Asn Phe Met Gln Gln
    130                 135                 140

Arg Gly Asn Phe Gly Ala Thr Tyr Arg Asn Thr Asp Phe Phe Gly Leu
145                 150                 155                 160

Val Asp Gly Leu Asn Phe Ala Val Gln Tyr Gln Gly Lys Asn Gly Asn
                165                 170                 175

Pro Ser Gly Glu Gly Phe Thr Ser Gly Val Thr Asn Asn Gly Arg Asp
            180                 185                 190

Ala Leu Arg Gln Asn Gly Asp Gly Val Gly Gly Ser Ile Thr Tyr Asp
        195                 200                 205

Tyr Glu Gly Phe Gly Ile Gly Gly Ala Ile Ser Ser Ser Lys Arg Thr
    210                 215                 220

Asp Ala Gln Asn Thr Ala Ala Tyr Ile Gly Asn Gly Asp Arg Ala Glu
225                 230                 235                 240

Thr Tyr Thr Gly Gly Leu Lys Tyr Asp Ala Asn Asn Ile Tyr Leu Ala
                245                 250                 255

Ala Gln Tyr Thr Gln Thr Tyr Asn Ala Thr Arg Val Gly Ser Leu Gly
            260                 265                 270

Trp Ala Asn Lys Ala Gln Asn Phe Glu Ala Val Ala Gln Tyr Gln Phe
        275                 280                 285

Asp Phe Gly Leu Arg Pro Ser Leu Ala Tyr Leu Gln Ser Lys Gly Lys
    290                 295                 300

Asn Leu Gly Arg Gly Tyr Asp Asp Glu Asp Ile Leu Lys Tyr Val Asp
305                 310                 315                 320

Val Gly Ala Thr Tyr Tyr Phe Asn Lys Asn Met Ser Thr Tyr Val Asp
                325                 330                 335

Tyr Lys Ile Asn Leu Leu Asp Asp Asn Gln Phe Thr Arg Asp Ala Gly
            340                 345                 350

Ile Asn Thr Asp Asn Ile Val Ala Leu Gly Leu Val Tyr Gln Phe
```

<210> SEQ ID NO 4
<211> LENGTH: 6
<212> TYPE: PRT
<213> ORGANISM: Artificial Sequence
<220> FEATURE:
<223> OTHER INFORMATION: synthetic polyhistidine tag, 6xHis tag, His-tag

<400> SEQUENCE: 4

His His His His His His
 1               5

<210> SEQ ID NO 5
<211> LENGTH: 1005
<212> TYPE: DNA
<213> ORGANISM: Artificial Sequence
<220> FEATURE:
<223> OTHER INFORMATION: synthetic pET-His-OmpA nucleotide sequence

<400> SEQUENCE: 5

```
atggcgcacc atcaccacca tcacgccgct ccgaaagata cacctggta cactggtgct      60 aaactgggct ggtcccagta ccatgatact ggtttcatca acaacaatgg cccgacccat    120
gaaaaccaac tgggcgctgg tgcttttggt ggttaccagg ttaacccgta tgttggcttt    180
gaaatgggtt acgactggtt aggtcgtatg ccgtacaaag cagcgttga aaacggtgca    240 tacaaagctc agggcgttca actgaccgct aaactgggtt acccaatcac tgacgacctg    300
gacatctaca ctcgtctggg tggcatggta tggcgtgcag acactaaatc caacgtttat    360
ggtaaaaacc acgacaccgg cgtttctccg gtcttcgctg cggtgttga gtacgcgatc    420 actcctgaaa tcgctacccg tctggaatac agtggacga caacatcgg tgacgcacac    480 accatcggca ctcgtccgga caacggcatg ctgagcctgg gtgtttccta ccgtttcggt    540
cagggcgagg cagctccagt agttgctccg gctccagctc cggcaccgga agtacagacc    600
aagcacttca ctctgaagtc tgacgttctg ttcaacttca caaagcaac cctgaaaccg    660 gaaggtcagg ctgctctgga tcagctgtac agccagctga gcaacttgga tccgaaagac    720
ggttccgtag ttgttctggg ttacaccgac cgcatcggtt ctgacgctta caaccagggt    780
ctgtccgagc gccgtgctca gtctgttgtt gattacctga tctccaaagg tatcccggca    840
gacaagatct ccgcacgtgg tatgggcgaa tccaacccgg ttactggcaa cacctgtgac    900
aacgtgaaac agcgtgctgc actgatcgac tgcctggctc cggatcgtcg cgtagagatc    960
gaagttaaag gtatcaaaga cgttgtaact cagccgcagg cttaa                   1005
```

<210> SEQ ID NO 6
<211> LENGTH: 334
<212> TYPE: PRT
<213> ORGANISM: Artificial Sequence
<220> FEATURE:
<223> OTHER INFORMATION: synthetic pET-His-OmpA amino acid sequence

<400> SEQUENCE: 6

Met Ala His His His His His His Ala Ala Pro Lys Asp Asn Thr Trp
 1               5                   10                  15

Tyr Thr Gly Ala Lys Leu Gly Trp Ser Gln Tyr His Asp Thr Gly Phe
            20                  25                  30

Ile Asn Asn Asn Gly Pro Thr His Glu Asn Gln Leu Gly Ala Gly Ala
        35                  40                  45

Phe Gly Gly Tyr Gln Val Asn Pro Tyr Val Gly Phe Glu Met Gly Tyr
    50                  55                  60

```
Asp Trp Leu Gly Arg Met Pro Tyr Lys Gly Ser Val Glu Asn Gly Ala
 65                  70                  75                  80

Tyr Lys Ala Gln Gly Val Gln Leu Thr Ala Lys Leu Gly Tyr Pro Ile
                 85                  90                  95

Thr Asp Asp Leu Asp Ile Tyr Thr Arg Leu Gly Met Val Trp Arg
                100                 105                 110

Ala Asp Thr Lys Ser Asn Val Tyr Gly Lys Asn His Asp Thr Gly Val
                115                 120                 125

Ser Pro Val Phe Ala Gly Val Glu Tyr Ala Ile Thr Pro Glu Ile
                130                 135                 140

Ala Thr Arg Leu Glu Tyr Gln Trp Thr Asn Asn Ile Gly Asp Ala His
145                 150                 155                 160

Thr Ile Gly Thr Arg Pro Asp Asn Gly Met Leu Ser Leu Gly Val Ser
                165                 170                 175

Tyr Arg Phe Gly Gln Gly Glu Ala Ala Pro Val Val Ala Pro Ala Pro
                180                 185                 190

Ala Pro Ala Pro Glu Val Gln Thr Lys His Phe Thr Leu Lys Ser Asp
                195                 200                 205

Val Leu Phe Asn Phe Asn Lys Ala Thr Leu Lys Pro Glu Gly Gln Ala
                210                 215                 220

Ala Leu Asp Gln Leu Tyr Ser Gln Leu Ser Asn Leu Asp Pro Lys Asp
225                 230                 235                 240

Gly Ser Val Val Val Leu Gly Tyr Thr Asp Arg Ile Gly Ser Asp Ala
                245                 250                 255

Tyr Asn Gln Gly Leu Ser Glu Arg Arg Ala Gln Ser Val Val Asp Tyr
                260                 265                 270

Leu Ile Ser Lys Gly Ile Pro Ala Asp Lys Ile Ser Ala Arg Gly Met
                275                 280                 285

Gly Glu Ser Asn Pro Val Thr Gly Asn Thr Cys Asp Asn Val Lys Gln
                290                 295                 300

Arg Ala Ala Leu Ile Asp Cys Leu Ala Pro Asp Arg Arg Val Glu Ile
305                 310                 315                 320

Glu Val Lys Gly Ile Lys Asp Val Val Thr Gln Pro Gln Ala
                325                 330

<210> SEQ ID NO 7
<211> LENGTH: 15
<212> TYPE: PRT
<213> ORGANISM: Artificial Sequence
<220> FEATURE:
<223> OTHER INFORMATION: synthetic N-terminal sequence of recombinant
      His-OmpA antigen

<400> SEQUENCE: 7

Ala His His His His His His Ala Ala Pro Lys Asp Asn Thr Trp
 1               5                  10                  15
```